US012784211B2

(12) United States Patent
Goldhagen

(10) Patent No.: US 12,784,211 B2
(45) Date of Patent: Nov. 3, 2026

(54) RETINAL DISTANCE-SCREENING USING MACHINE LEARNING

(71) Applicants: UNITED STATES GOVERNMENT AS REPRESENTED BY THE DEPARTMENT OF VETERANS AFFAIRS, Washington, DC (US); UNIVERSITY OF MIAMI, Miami, FL (US)

(72) Inventor: Brian Goldhagen, Tampa, FL (US)

(73) Assignees: United States Government as Represented by the Department of Veterans Affairs, Washington, DC (US); University of Miami, Miami, FL (US)

( * ) Notice: Subject to any disclaimer, the term of this patent is extended or adjusted under 35 U.S.C. 154(b) by 209 days.

(21) Appl. No.: 18/855,947

(22) PCT Filed: Apr. 12, 2023

(86) PCT No.: PCT/US2023/018296

§ 371 (c)(1),
(2) Date: Oct. 10, 2024

(87) PCT Pub. No.: WO2023/200846

PCT Pub. Date: Oct. 19, 2023

(65) Prior Publication Data

US 2025/0252561 A1 Aug. 7, 2025

Related U.S. Application Data

(60) Provisional application No. 63/331,538, filed on Apr. 15, 2022.

(51) Int. Cl.
*G06T 7/00* (2017.01)
*A61B 3/00* (2006.01)
(Continued)

(52) U.S. Cl.
CPC .......... *G06T 7/0012* (2013.01); *A61B 3/0025* (2013.01); *A61B 3/12* (2013.01);
(Continued)

(58) Field of Classification Search
CPC ......... G06T 7/0012; G06T 2207/20081; G06T 2207/30041; G06T 2207/20021; G06T 2207/20084; G06T 7/0014; G06T 5/00; G06T 5/50; G06T 7/00; G06T 7/37; G06T 7/0016; G06T 11/00; G06T 11/008; G06T 2207/10101; G06T 2207/10084; G06T 2207/20016; G06T 3/4046; G06T 5/60; G06T 9/002; G06T 2207/20076; G06T 2211/441; A61B 3/0025; A61B 3/12; A61B 3/10; A61B 3/102; G06V 10/764;
(Continued)

(56) References Cited

U.S. PATENT DOCUMENTS 8,879,813 B1 * 11/2014 Solanki ................ A61B 3/0025 382/128
11,883,099 B2 * 1/2024 Jia ............................. G06T 7/62
(Continued)

*Primary Examiner* — Jose L Couso
(74) *Attorney, Agent, or Firm* — Ballard Spahr LLP

(57) ABSTRACT

Methods, systems, and apparatuses are provided for retinal distance-screening using machine learning.

20 Claims, 12 Drawing Sheets

(51) Int. Cl.

| | |
|---|---|
| ***A61B 3/12*** | (2006.01) |
| ***G06V 10/764*** | (2022.01) |
| ***G06V 10/774*** | (2022.01) |
| ***G16H 30/40*** | (2018.01) |

(52) U.S. Cl.

CPC .......... *G06V 10/764* (2022.01); *G06V 10/774* (2022.01); *G16H 30/40* (2018.01); *G06T 2207/20081* (2013.01); *G06T 2207/30041* (2013.01); *G06V 2201/03* (2022.01)

(58) Field of Classification Search

CPC .. G06V 10/774; G06V 2201/03; G06V 10/26; G06V 10/993; G06V 40/18; G06V 10/454; G06V 10/54; G06V 10/70; G06V 10/82; G06V 10/84; G06V 20/41; G06V 30/18057; G06V 20/698; G06V 30/19173; G06V 30/194; G16H 30/40; G16H 50/30; G16H 20/40; G16H 50/20; G06N 3/02; G06N 3/08–088; G06N 3/04; G06N 3/0445; G06N 3/0454; G06N 3/0464; G06N 3/0475; G06N 3/4046; G06N 3/4053; G06N 3/049; G06N 3/0499; G06N 7/00; G06N 7/01; G06N 20/00; G06K 7/1482; G06F 18/213; G06F 18/214; G06F 18/22; G06F 18/241; G06F 18/24; G06F 18/2411; G06F 18/2415; G06F 18/253; G06F 30/27; G05B 2219/25255; G05B 2219/41054; Y10S 128/925

See application file for complete search history.

(56) References Cited

U.S. PATENT DOCUMENTS

| | | | | |
|---|---|---|---|---|
| 2012/0249959 | A1* | 10/2012 | You | G06V 40/18 351/246 |
| 2015/0124216 | A1 | 5/2015 | Abramoff et al. | |
| 2019/0110753 | A1* | 4/2019 | Zhang | G06N 3/084 |
| 2020/0342595 | A1* | 10/2020 | Jia | G06N 3/08 |
| 2021/0158525 | A1* | 5/2021 | Iwase | A61B 3/0025 |
| 2021/0319556 | A1* | 10/2021 | Chauhan | G06T 7/0014 |
| 2022/0058803 | A1 | 2/2022 | Bhattacharya et al. | |
| 2022/0084197 | A1 | 3/2022 | Wyder et al. | |
| 2023/0410293 | A1* | 12/2023 | De Sisternes | G06T 7/0012 |
| 2024/0306908 | A1* | 9/2024 | Koronyo | A61B 3/10 |

* cited by examiner

A

B

| | Image Quality | | | | Assessment | |
|---|---|---|---|---|---|---|
| | Macula | Nasal | Superior | Nerve | Retinopathy | Other |
| Right | PASS | PASS | PASS | PASS | PRESENT | PASS |
| Left: | PASS | PASS | PASS | PASS | PRESENT | PRESENT |

A

| File Name | Location | Retinopathy | Other Findings |
|---|---|---|---|
| ******.DCM | Right Macula | Present | |
| ******.DCM | Right Superior | Absent | |
| ******.DCM | Right Nasal | Absent | |
| ******.DCM | Left Macula | Absent | Drusen |
| ******.DCM | Left Superior | Absent | |
| ******.DCM | Left Nasal | Present | |
| ******.DCM | Iris | N/A | |
| ******.DCM | Iris | N/A | |

RETINAL DISTANCE-SCREENING USING MACHINE LEARNING

CROSS-REFERENCE TO RELATED APPLICATIONS

This Application is a national stage filing under 35 U.S.C. § 371 of International Application No. PCT/US2023/018296, filed on Apr. 12, 2023, which claims priority to U.S. Provisional Application No. 63/331,538, filed Apr. 15, 2022, both of which are incorporated by reference herein in their entireties.

BACKGROUND

Diabetic retinopathy is a leading cause of blindness in some segments of the population, such as working-age adults. Retinal distance-screening (or teleretinal screening) has been used to diagnose diabetic retinopathy. As part of this screening, retinal images are captured at a local patient site and are read by eye care professionals at a separate site that is remotely located relative to the local patient site. The patient is then referred for an in-person, face-to-face eye examination if retinopathy is detected in the retinal images. Continuously increasing demand for retinal distance-screenings and the ability of these eye care professionals that evaluate retinal images to provide a higher level of care have created inefficiencies in the implementation of retinal distance-screening. Therefore, much remains to be improved in technologies for retinal distance-screening.

SUMMARY

It is to be understood that both the following general description and the following detailed description are illustrative and explanatory only and are not restrictive.

Technologies disclosed herein, individually or in combination, provide a sensitive screening tool that utilizes machine learning to identify ocular abnormalities in retinal photos, differentiating normal fundus photos from abnormal fundus photos. Examples of the ocular abnormalities that can be identified include diabetic retinopathy, macular degeneration, and glaucoma. Technologies disclosed herein, individually or in combination can be used as a retinal distance-screening product or can be integrated into existing retinal distance-screening platforms. In some implementations, a list of patients can be obtained, retinal images pertaining to the patients in the list can be designated as either normal or abnormal, and results of such classification can be supplied for further analysis. The technologies described herein also can be implemented to pre-screen patients into those that need further assessment by our trained optometrists and those that do not need further assessment.

Integration of the disclosed technologies into existing retinal distance-screening platforms can be accomplished by means of a digital imaging and communications in medicine (DICOM) receiver module that is integrated into a server device having modules for analysis of retinal images using machine learning in accordance with aspects described herein. The server device can receive, via the DICOM received module, for example, retinal images of one or both eyes of a patient. The modules for analysis can assess one or more of the retinal images and can retain results of the assessment in a database and/or a file within data storage. A client device can access the results from the data storage by executing a client application. The client device can present the results to a reviewer agent for confirmation and/or further examination of the retinal images.

The technologies described herein improve upon current standard of care by means of the utilization of computing devices and computer-implemented methods to screen retinal photos. An example of improvement over existing technologies includes the availability of assessed retinal images to a human agent (an optometrist or an ophthalmologist) for confirmation of findings or a secondary review. Hence, the technologies described herein provide greater safety for patients have overall superior results than existing technologies. Another example of improvement over existing technologies includes the customization to a particular population of patients or other types of subjects. Such a customization can be achieved by generating training and validation datasets that are specific to the particular population. In one example, the technologies described herein can be customized for the U.S. veteran population and/or other populations having defined race and/or ethnicity. In another example, the technologies described herein can be customized for subjects who are candidates for military service, police training, or another type of security forces. Yet another example of improvement over existing technologies includes the detection of a wide variety of ocular diseases that extends beyond diabetic retinopathy. The technologies described herein can detect macular degeneration and glaucoma, in addition to diabetic retinopathy.

Further in contrast to existing technologies, the technologies described herein can readily adopt well-established telehealth guidelines for distance-screening programs. As such, the assessments of retinal images obtained using the technologies described herein can result in less referrals for face-to-face exams, with ensuing greater provider efficiency.

Additional elements or advantages of this disclosure will be set forth in part in the description which follows, and in part will be apparent from the description, or may be learned by practice of the subject disclosure. The advantages of the subject disclosure can be attained by means of the elements and combinations particularly pointed out in the appended claims.

This summary is not intended to identify critical or essential features of the disclosure, but merely to summarize certain features and variations thereof. Other details and features will be described in the sections that follow. Further, both the foregoing general description and the following detailed description are illustrative and explanatory only and are not restrictive of the embodiments of this disclosure.

BRIEF DESCRIPTION OF THE DRAWINGS

The annexed drawings are an integral part of the disclosure and are incorporated into the subject specification. The drawings illustrate example embodiments of the disclosure and, in conjunction with the description and claims, serve to explain at least in part various principles, elements, or aspects of the disclosure. Embodiments of the disclosure are described more fully below with reference to the annexed drawings. However, various elements of the disclosure can be implemented in many different forms and should not be construed as limited to the implementations set forth herein. Like numbers refer to like elements throughout.

DETAILED DESCRIPTION

Figure 1:
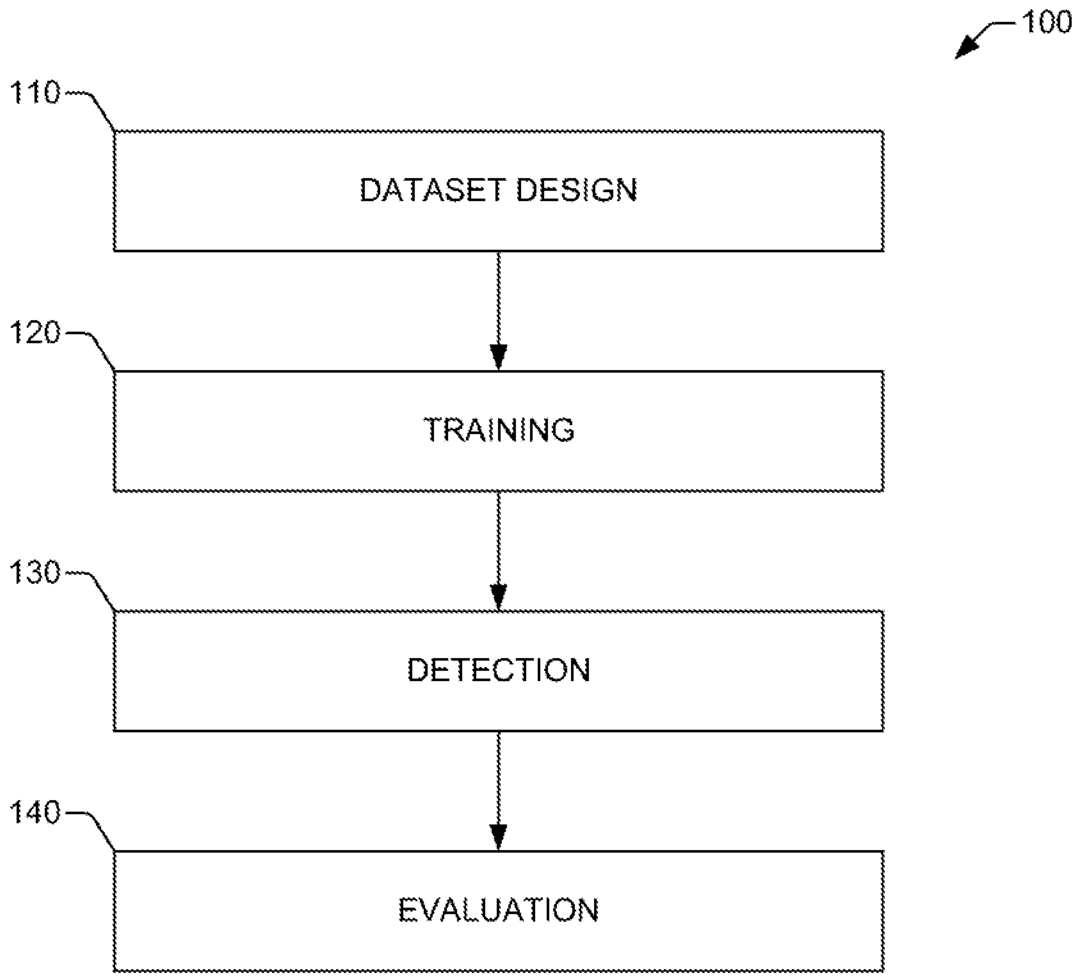
FIG. 1 illustrates an example of a process flow for retinal distance-screening using machine learning, in accordance with one or more embodiments of the disclosure.

The disclosure recognizes and addresses, among other technical challenges, the issue of evaluation of retinal images for presence of ocular abnormalities. Evaluation of retinal images can pose many challenges. Among those challenges, many existing algorithms that exist, particularly those currently FDA approved, do not use the same high standards for referral for a face-to-face exam as those used by other entities, such as the VHA teleretinal screening program. Terms including referable diabetic retinopathy and vision-threatening retinopathy are utilized, which permit for a greater margin of error for algorithms used in the detection of diabetic retinopathy by grouping those patients with mild nonproliferative diabetic retinopathy (NPDR) with normal patients with diabetes. However, while allowing for the impression of a better algorithm performance, it also may result in a reduction in the standard of care that is provided by some of the existing teleretinal screening programs.

Embodiments of this disclosure can implement retinal distance-screening (which also can be referred to as teleretinal screening) using machine learning. To that end, various types of machine-learning models can be generated. A first machine-learning model can be generated to determine a retina region that is depicted in a retinal image. Second machine-learning models can be generated to determine quality of retinal images, where the second machine-learning models are specific to respective types of regions that can be depicted in a retinal image. The quality of a retinal mage can represent a gradeability of the retinal image. Such gradeability can be defined in terms of various image attributes that, based on their values, can permit or preclude evaluation of the retinal image. A third machine-learning model also can be generated to detect various types of objects within a retinal image. At least some of the objects that can be detected are ocular abnormalities.

After a region of a retina has been determined by applying the first machine-learning model to a retinal image, one of the second machine-learning models can be applied to the retinal image in order to determine quality of that image. The second machine-learning model that is applied has been trained to evaluate gradeability of retinal images depicting the region identified by the first machine-learning model. In cases where the gradeability is satisfactory, the third machine-learning model can be applied to detect one or more objects within the retinal image.

Respective attributes of the object(s) that may have been detected can be evaluated in order to designate the retinal image as presenting retinopathy or not presenting retinopathy. The respective attributes can include confidence scores, and the evaluation can include comparison of the confidence scores with a threshold value. The evaluation also can include determining numbers of detected ocular abnormalities in a retinal image. A retinal image that is designated as presenting retinopathy can be augmented with metadata. The resulting augmented retinal image can be supplied for confirmation of a diagnosis of retinopathy and/or further evaluation of the augmented retinal image.

It is noted that co-existing retinal findings not readily apparent on a retinal distance-screening are more likely to be present in eyes of patients afflicted by mild NPDR. For example, in the case of mild NPDR that embodiments of this disclosure determined to require additional review, hollenhorst plaques were also found to be present. Hollenhorst plaques not only have a refractile nature that has the potential to make it easier to identify them on face-to-face exam, but also may be present in regions of the retina not captured in original photographs of the eyes. Once identified, a referral for a carotid ultrasound would typically be recommended to assess for potential stenosis, which depending on its severity, may necessitate surgery. An algorithm that would have grouped mild NPDR as normal and that did not assess for other ocular findings that may be present would have allowed this patient to go without receiving appropriate care until a next preventative screening.

FIG. 1 illustrates an example of a process flow 100 for the development and application of machine-learning (ML) models for the detection of ocular abnormalities within a retinal distance-screening program. The process flow 100 can be used to manage, enhance, and assess retinal images for presence or absence of various types of ocular abnormalities. The process flow 100 includes multiple stages, represented by respective blocks in FIG. 1, that can be implemented individually or in combination. The retinal images involved in the process flow 100 may, in some cases, be lower quality images relative to digital images that are typically used in the development and utilization of machine-learning techniques.

A retinal distance-screening event to assess a retinal condition of a patient includes the acquisition of multiple retinal images from the patient in a single day. In this disclosure, the multiple retinal images from the patient on that single day are referred to as an "image set." An image set can contain a particular number of external ocular images and a particular number of retinal images. An external ocular image can include other parts of the eye visible in the image besides the iris (or colored part of the eye). More specifically, an external ocular image can depict ocular adnexa (e.g., eyelids) and the anterior segment of the eye. The anterior segment of the eye can include the iris as well as the cornea, conjunctiva, and lens. The total number of images in such an image set can range from eight to 18 images, for example. A typical composition of that image set can include two external ocular images and eight retinal images. External ocular images can be excluded from the machine-learning approaches described herein. In some cases, image sets may exclude external ocular images. The multiple retinal images in the image set are directed to capturing various regions of the undilated eye in adequate quality, as is stipulated in a defined retinal distance-screening protocol. In some cases, an image set may be acquired for dilated eyes. Such a protocol can be the teleretinal screening protocol set forth by the U.S. Department of Veterans Affairs, for example. Those various regions include macula region of retina, superior region of retina, and nasal region of retina. The defined retinal distance-screening protocol can dictate that the optic nerve be observed in at least one retinal image per eye. Per the defined retinal distance-screening protocol, multiple photos of a particular region can be obtained, resulting in more than eight retinal images. To satisfy quality rules stipulated in the defined retinal distance-screening protocol, the multiple retinal images can be acquired such that shadows and other artifacts are positioned in different regions of a retinal image, across the multiple retinal images in the image set.

Diabetic abnormalities that may be present and can be detected on an image set include hemorrhages and exudates. Other forms of ocular abnormalities may still exist and also can be detectable on the image set.

The process flow 100 includes a dataset design stage 110 where one or several datasets of retinal images can be generated for the training of machine-learning models for a retinal distance-screening program. Transfer learning techniques, using pre-trained architectures, can be utilized in the development of an ML model to detect ocular abnormalities. The development of a learning dataset of retinal images for the application of such transfer learning techniques differs from typical dataset development used in existing machine-learning technologies. In commonplace dataset development, a dataset is randomly split into two or three subsets: training subset, testing subset, and sometimes, a validation subset. An issue with randomly splitting the dataset is that although an ML model is neither tested nor validated on the same retinal images on which the ML model was developed, retinal images in each one of the testing subset and the validation subset actually represent a random sampling from the same sample of the population on which the ML model has been trained. As such, the testing/validation in the traditional manner may not yield an ML model that is readily generalizable to future imaging events.

Figure 2A:
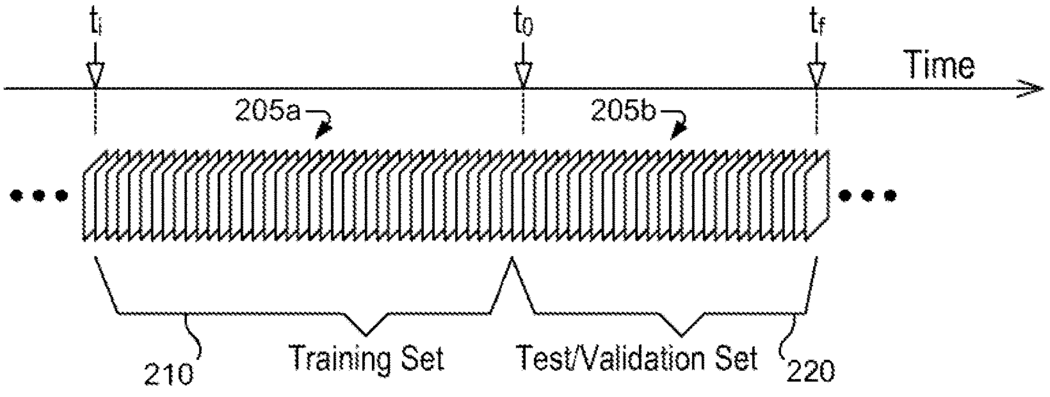
FIG. 2A illustrates an example of an approach to partition multiple image sets into a training set and a validation set to train a machine-learning model, in accordance with one or more embodiments of the disclosure.

As is illustrated in FIG. 2A, in the development of the ML models of this disclosure, two chronologically separated datasets were respectively assigned to a training set 210 and testing/validation set 220. Thus, instead of obtaining retinal images 205*a* from a first time interval $t_0$-$t_i$ (e.g., one month) and splitting those images into a training subset and testing subset (e.g., a 70/30 random split), the retinal images 205*a* from the first time interval are assigned to the training set 210 and retinal images 205*b* from a second time interval $t_f$-$t_0$ (e.g., another month) subsequent to the first time interval are assigned to the testing/validation set 220. In that way, it can be ensured that no duplicate patients are present in both the first and second time intervals. It is noted that in some cases, the training set 210 and the testing/validation set 220 can be probed for presence of duplicate patients, with detected duplicate patient(s) being removed from either one of those sets. Probing the training set 210 and the testing/validation set 220 in such a fashion can include automatically reviewing a list of patients to ensure that the same patient is include in only one of those two sets. Such an approach to learning-dataset development can avoid having images from a same patient in both the training set 210 and the testing/validation set 220, and also can provide a more accurate way of testing how an ML model may operate on imaging data if used prospectively within a particular population in the present and in the future. Such an ML model can be a detection model that has been trained to detect ocular abnormalities, for example.

Various ML models can be generated in a training stage 120 of the process flow 100 (FIG. 1). Some of the ML models that are trained can be used to generate learning datasets having adequate retinal images. As mentioned, those machine-learning models can be trained using transfer learning techniques. An adequate retinal image is a retinal image that corresponds to a defined ocular region (e.g., macula, superior, or nasal) and has satisfactory fitness for subsequent analysis. Satisfactory fitness can be dictated by gradeability. In this disclosure, "gradeability" refers to an attribute of a retinal image that renders the image satisfactory or unsatisfactory for evaluation of presence or absence of an ocular abnormality. For example, the retinal image is unsatisfactory when one or both of the following criteria are met: (1) Poor photographic quality or obscuration from media opacity or small pupils, or other abnormality makes it difficult to determine whether a lesion or abnormality is present. (2) If three or more "magnified areas" of retina are not visible in photographic field. It is noted that three or more magnified areas within a photographic field is essentially equivalent to approximately four to six disc diameters.

Based on a training dataset and testing/validation dataset, a ML model can be trained, using transfer learning techniques, to identify a region depicted in each image in an image set—left macula, right macula, left superior, right superior, left nasal, right nasal, or ocular adnexa and anterior segment of the eye—in a dataset. Such an ML model can be referred to as locus model. By applying the locus model, images depicting respective regions identified as external ocular region(s) can be removed from subsequent analysis. Thus, the locus model can be applied to images of an image set as a filter, removing images depicting external ocular region(s) (e.g., an iris) and yielding retinal images depicting macula, superior, or nasal regions. The training dataset and the testing/validation dataset can include labeled data identifying a particular region (macular, superior, or nasal) of each retina image in those datasets. The labeled data can be human-labeled by optometrists that serve as readers of retinal images pertaining to an existing retinal distance-screening program. In addition, or in some cases, other suitable human agents can generate the labeled data.

Also based on a training dataset and testing/validation dataset, a second ML models can be trained, using transfer learning techniques, to determine gradeability of a retinal image depicting either one of the macula, superior region, or nasal region. Such a second ML model can be referred to as fitness model. Three fitness models can be trained: a first fitness model corresponding to macula region, a second fitness model corresponding to superior region, and a third fitness model corresponding to the nasal region. The training dataset and the testing/validation dataset can include labeled data identifying gradeability of each retina image in those datasets. Again, the labeled data can be human-labeled by optometrists that serve as readers of retinal images pertaining to an existing retinal distance-screening program. In addition, or in some cases, other suitable human agents can generate the labeled data.

Performance of a fitness model can be improved by updating labeled retinal images to primarily depict respective areas of interest before training the fitness model. Updating a labeled retinal image can include cropping the retinal image to the area of interest (e.g., macula, superior, or nasal). For example, a retinal image that depicts the superior region can be cropped to exclude a bottom part of the image because that part contains the macula region. The retina image can be cropped in such a fashion because the macula region is subjected to a gradeability assessment in a different retinal image, using a fitness model corresponding the macula region. In addition, or some cases, prior to training a fitness model, image augmentations can be applied to labeled retinal images in an appropriate manner for each type of retinal image.

For example, the augmentations can include flipping, magnification, rotation, a combination thereof, or similar. Thus, in some cases, augmenting retinal images can include operating on the retinal images by applying a reflection operation about a defined plane to least one of the retinal images; applying a rotation operation about a defined axis to the at least of the retinal images; magnifying by a defined factor the at least one of the retinal images, or cropping the at least one of the retinal images to exclude defined pixels. It is noted that horizontal flipping was not used for determination of location because ophthalmologists use this information to determine whether they are looking at a left eye or a right eye.

Multiple retinal images generated during a defined period (e.g., $t_f$-$t_i$ in FIG. 2A) can form a candidate learning-dataset to train a third ML model to determine presence or absence of ocular abnormalities in an image set (that is, multiple retinal images from a patient obtained on a single day). The third ML model can be referred to as a detection model. The candidate learning-dataset can include retinal images depicting defined ocular abnormalities (e.g., intraretinal hemorrhages and exudates) with a quality that exceeds that of retinal images obtained in existing retinal distance-screening programs. For example, the retinal images that constitute the candidate learning dataset can includes images depicting high-quality representative examples of each ocular abnormality of interest from an in-person ophthalmologic clinical practice.

Prior to training the detection model, during implementation of the dataset design stage 110, the trained locus model and at least one trained fitness model can be applied to the candidate learning subset to eliminate retinal images having unsatisfactory gradeability. The trained locus can distinguish external ocular images from retinal images. Application of such models can yield a satisfactory learning dataset. The satisfactory learning dataset can be divided into a training set and a testing/validation set in accordance with aspects of this disclosure, as is described herein in connection with FIG. 2A, for example. That satisfactory learning dataset is used to train the detection model.

In the training stage 120, the detection model can be trained using the satisfactory learning dataset and transfer learning techniques with pre-trained "object detection" architectures. In that way, ocular abnormalities having small size relative to the entire size of a retinal image can be more readily detected using the trained detection model. As an example, the detection model can be trained using transfer learning techniques based on a COCO-pretrained SSD with EfficientNet and bi-directional feature pyramid network (BiFPN) feature extractor. As another example, the detection model also can be trained using a single-stage detector based on you look only once (YOLO) convolutional neural network (CNN) architecture.

The detection model can be trained to solve a multi-task classification problem using imaging data defining retinal images. Thus, the trained detection model can detect one or multiple objects within each retinal image in an image set. Each one of the detected object(s) corresponds to a type of object within a defined group of objects. A detected object can be identified as part of solving the multi-task classification problem. The detected object can be identified by designating the detected object as being of a particular type—e.g., an intraretinal hemorrhage, particulate matter, a cotton-wool spot, drusen, or optic nerve—and generating a confidence score for such a classification. To that end, the trained detection model can generate a label (e.g., a string of characters) identifying the detected object. As part of solving the multi-task classification problem, the trained detection model also can generate a confidence score that quantifies a probability that such an identification is a ground-truth observation.

Besides training a detection model directly for detection of ocular abnormalities, the detection model also can be trained to identify other objects that may appear similar to ocular abnormalities within a retinal image. Such a refinement can permit the detection model to distinguish between an object corresponding to an ocular abnormality and another object corresponding to an artifact. More specifically, the detection model can be trained to distinguish between an ocular abnormality and an object that could be confounded with the ocular abnormality. For example, the fovea is the reddish circular center of the macula and, thus, without adequate training, a detection model may confound the fovea with a reddish circular hemorrhage. Accordingly, as part of the training stage 120, the fovea can be labeled within a learning dataset of retinal images, and the detection model can be trained to identify the fovea within a retinal image as a particular type of object. As another example, "dust" and a hemorrhage also may be confounded by a detection model without adequate training. Accordingly, as part of the training stage 120, "dust" can be labelled within a learning dataset, and a detection model can be trained to identify "dust" as a separate type of object within a retinal image. By training the detection model to identify the fovea and/or dust among other objects, the trained detection model may better discern between dust and a hemorrhage.

Various other approaches can be incorporated into the training stage 120. Those approaches can improve the use of available computational resources. For example, computer memory constraints may be present in a computing device or a system of computing devices that can implement the process flow 100 in its entirety or partially. Addressing such an issue by resizing retinal images to sizes smaller than their original sizes may render the detection of small abnormalities difficult. One approach that avoids resizing a retinal image includes cropping the retinal image to remove empty back space around the retinal image.

A more efficient approach that also avoids resizing the retinal image includes utilizing a tiling technique that can retain the original resolution by splitting the retinal image into multiple smaller images. The smaller images can be referred to as tile images. Each one of such tile images has the same image quality as the originating retinal image. The tiling technique can maintain image quality while decreasing computer memory demand in training a detection model. Additionally, the tiling technique can permit training the detection model to train on higher quality retinal images compared to downsized retinal images. Maintaining image quality may permit the trained detection model to detect small objects. A small object can have a characteristic length of a few pixels. As an example, instead of resizing a 300×300 pixel retinal image (which may be referred to as an originating image) into a single 100×100 image, that originating image can be split into nine 100×100 tile images. Each one of the 100×100 tile images has the same image quality as the originating image.

Figure 2B:
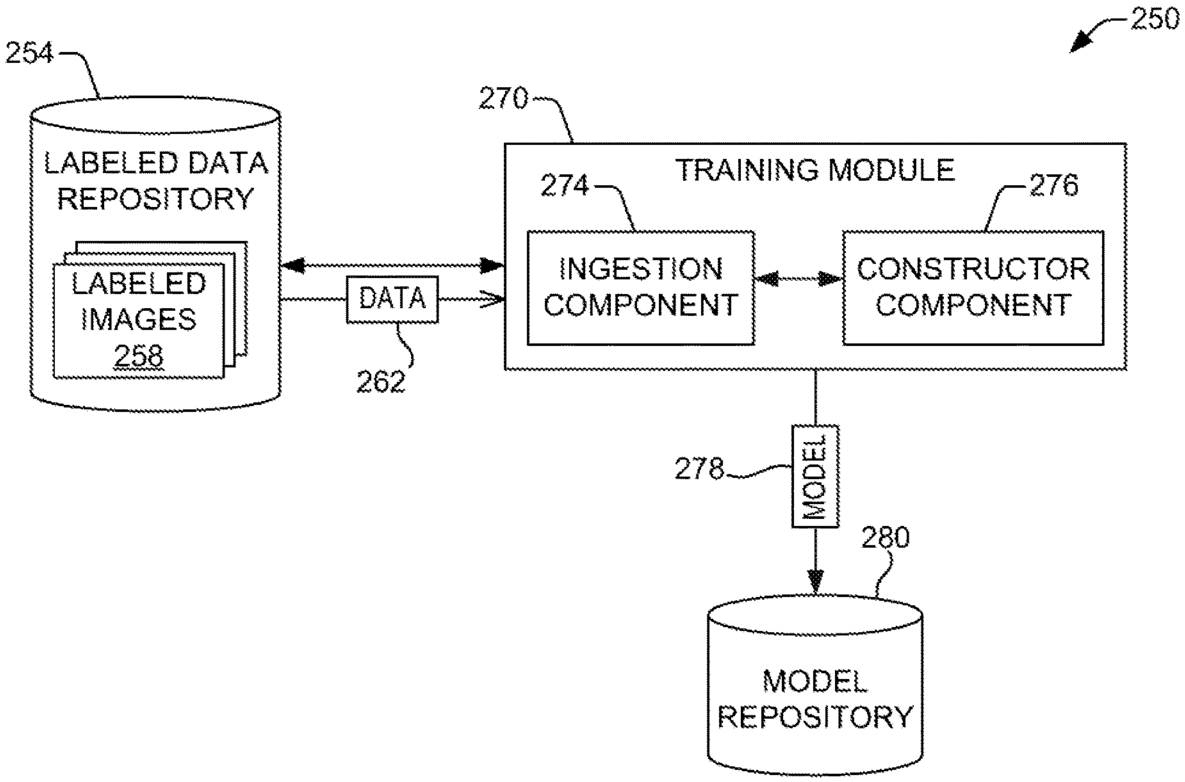
FIG. 2B illustrates an operating environment for generation of a detection model configured to identify multiple objects in a retinal image, in accordance with one or more embodiments described herein.

FIG. 2B illustrates an example of an operating environment 250 to generate a detection model, in accordance with one or more embodiments described herein. As mentioned, the detection model can be embodied in a CNN model. The operating environment 250 can include a training module 270. The training module 270, via an ingestion component 274, for example, can obtain different types of training data. Because the detection model can be generated to solve a multi-task classification problem on a retinal image, the ingestion component 274 can obtain labeled data 262 from one or more memory devices 254 (referred to as labeled data repository 254). The labeled data 262 can define multiple labeled retinal images from a group of several labeled images 258. In order to maintain image quality and present memory resources, each one of those multiple labeled retinal images can be a tile image having one or multiple labeled objects. The objects may have been labeled by a human agent, for example. A label of a labeled object can include one or a combination of a textual element and a graphical element. Each label for the labeled object(s) in a tile image designates a type of object—e.g., an intraretinal hemorrhage, particulate matter, a cotton-wool spot, drusen, or optic nerve.

The training module 270 also includes a constructor component 276 that can operate on the data 262 obtained by the ingestion component 274. By operating on the data 262, the constructor component 620 can train the detection model using at least a subset of the labeled images 258. As mentioned, the detection model can be trained to designate an object as pertaining to one of multiple categories, each category represents a type of object. To train the classification model, the constructor component 276 can determine, using the data 262, a solution to an optimization problem with respect to a cost function. The solution can be determined iteratively, and the cost function yields a value based on an evaluation of differences between known labels for respective objects and predicted labels for the respective objects. The predicted labels being predicted by an iteration of the detection. After a solution has been determined, the solution results in model parameters that minimize the cost function. The model parameters define a trained detection model 278. The training module, via the constructor component 276, for example, can retain the trained classification model 278 in one or more memory devices 280 (referred to as model repository 280).

The example process flow 100 includes a detection stage 130 where a trained detection model can be applied to an image set received from a patient under evaluation. Application of the trained detection model to the image set results in the identification of one or multiple objects within the image set. At least one of the multiple objects can be an ocular abnormality. Additionally, application of the trained detection model also generates a confidence score for the identification (or classification). As is described herein, the trained detection model can solve a multi-task classification problem using imaging data defining the retinal image.

Figure 3:
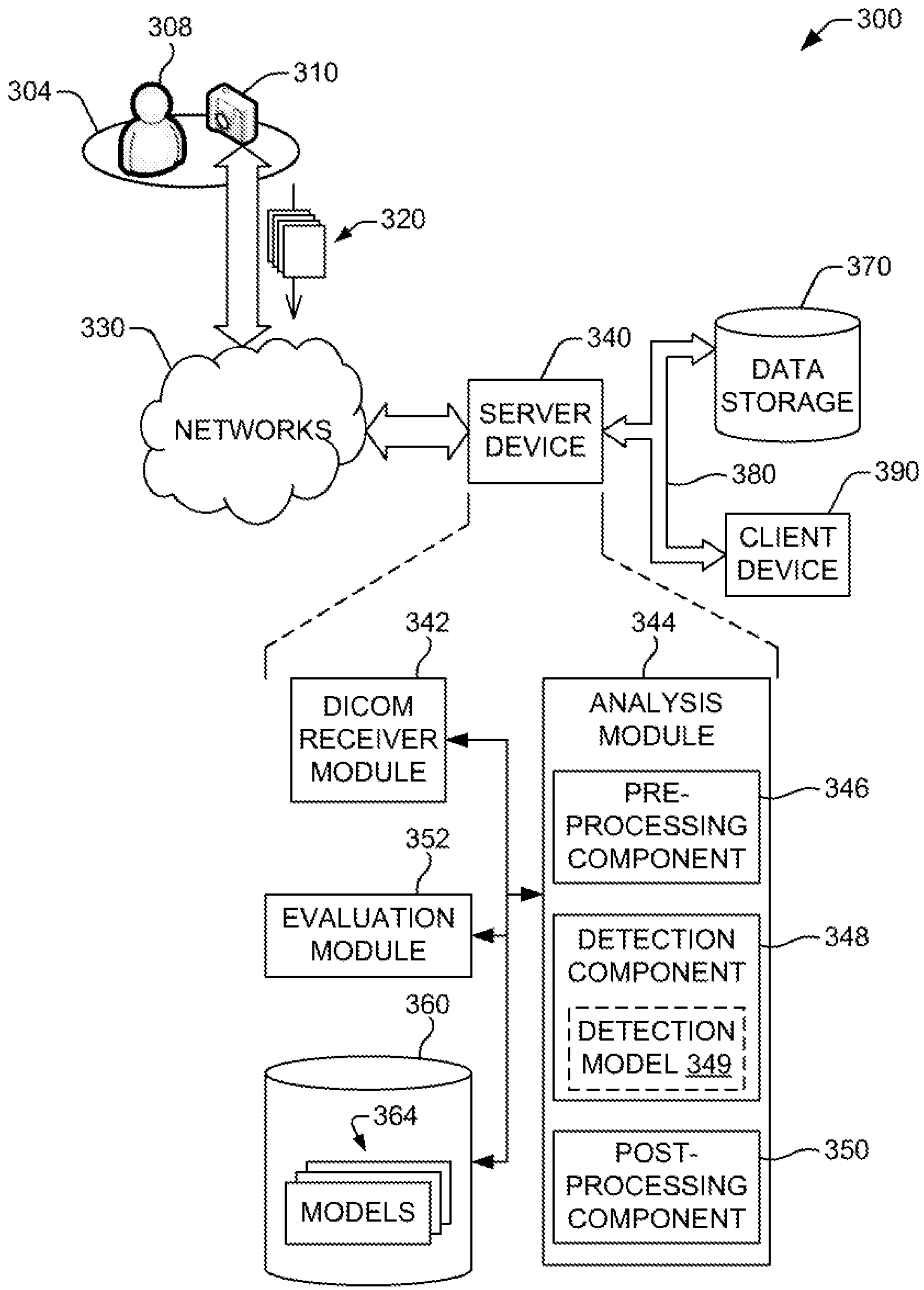
FIG. 3 illustrates an example of an operating environment for retinal distance-screening using machine learning, in accordance with one or more embodiments of the disclosure.

The detection stage 130 can be implemented in an example operating environment 300 as is shown in FIG. 3. In the example operating environment 300, a patient 308 can be located at an acquisition site 304, such as a dwelling of the patient 308, a screening site, or a medical facility. Such a dwelling can be a house of the patient, a group home, or an assisted living facility, for example. A screening site can be ad hoc location, such as a library, a supermarket, a pharmacy, a recreational community center, or similar. The acquisition site 304 may be referred to as a point of care. A camera device 310 can acquire multiple retinal images of one eye or both eyes of the patient 308. Acquiring the multiple retinal images includes generating imaging datasets defining respective ones of the multiple retinal images. An imaging dataset can be formatted according to a particular imaging standard, such as the DICOM standard. Other types of formats also can be contemplated.

The multiple retinal images form an image set 320. In some cases, a first subset of multiple retinal images corresponds to an eye of the patient 308, and a second subset of the multiple retinal images corresponds to the other eye of the patient 308. As any other image set of this disclosure, the image set 320 contains a particular number of retinal images, ranging from eight to 18 images in some cases.

The camera device 310 can send the image set 320 to a server device 340 via one or more networks 330. The server device 340 can be remotely located relative to the acquisition site 304. For example, the server device 340 can be located at a campus of hospital. Each one of networks in the network(s) 330 can include wired link(s) and/or wireless link(s) and several network elements that form a communication architecture having a defined footprint. The network elements can include, for example, base stations, access points, routers or switches, concentrators, servers, and the like. The network(s) 330 can be embodied in a local area network (LAN), a metropolitan area network (MAN), a wide area network (WAN), or a combination thereof.

Sending the image set 320 includes sending the imaging datasets defining the retinal images that form the image set 320. The server device 340 can receive the image set 320 via a DICOM receiver module 342 integrated into the server device 340. In some cases, the DICOM receiver module 342 can be functionally coupled to, but separate from, the server device 340.

The DICOM receiver module 342 can provide the image set 320 to an analysis module 344. To that end, the DICOM receiver module 342 can provide the image datasets that form the image set 320 to the analysis module 344. In one configuration, the DICOM receiver 342 can send the image datasets in respective communications, where a current image dataset is sent after the analysis module 344 has processed a prior image dataset. In other words, the DICOM receiver 342 can provide one retinal image at a time, for processing at the analysis module 344.

The analysis module 344 can receive an imaging dataset defining a retinal image of the image set 320. The analysis module 344 can include a pre-processing component 346 that can apply a locus model to the imaging dataset to determine a region of the retina depicted by the retinal image. That region can be the macula, superior region, or nasal region. The locus model is a machine-learning model that has been trained in accordance with aspects of this disclosure. The pre-processing component 346 can obtain the locus model from a group of multiple machine-learning models 364 retained within memory 360. Such a group can be arranged a database containing machine-learning models or a filesystem that contains files defining machine-learning models. The memory 360 can be embodied in multiple memory devices including a combination of non-volatile memory and volatile memory. The memory 360 can be arranged in main memory and mass storage.

Additionally, the pre-processing component 346 can apply a fitness model to the imaging dataset to determine gradeability of the retinal image defined by the imaging dataset. The fitness model can be specific to the region of the retina (macula, superior, or nasal) identified by the locus model. In other words, the pre-processing component 346 can determine, using the fitness model, if such the retinal image is gradable. To that end, the pre-processing component 346 can determine if the gradeability satisfies a selection criterion for further analysis of the retinal image. That further analysis can include detection of one or multiple ocular objects within the retinal image. As mentioned, the fitness model is a machine-learning model that has been trained in accordance with aspects of this disclosure. The pre-processing component 346 can obtain, using identification data generated by the locus model, the fitness model from the group of machine-learning models 364.

In response to the gradeability satisfying the selection criterion, the pre-processing component 346 can provide the imaging dataset to a detection component 348. The detection component 348 can obtain a detection model 349 that has been trained to identify one or multiple objects within a retinal image. The detection model 349 can be, for example, a multi-task classification model that has been configured according to transfer learning techniques using pre-trained structures, as is described herein. The detection component 348 can obtain the detection model 349 from the group of machine-learning models 364.

The detection component 348 can determine presence of multiple ocular abnormalities by applying the detection model 349 to the retinal image defined by the imaging dataset. Applying the detection model 349 yields a first confidence score for a first one of the multiple ocular abnormalities and a second confidence score for a second one of the multiple ocular abnormalities. The first confidence score quantifies the likelihood that the first one of the multiple ocular abnormalities is a ground-truth observation. Likewise, the second confidence score quantifies likelihood that the second one of the multiple ocular abnormalities is another ground-truth observation.

The analysis module 344 can continue processing imaging datasets defining respecting retinal images until the entire image set has been processed. The implementation of operations corresponding to the processing of the image set can be referred to as a detection event.

In the detection stage 130 (FIG. 1), due to the tiling that may be applied during the training of a detection model of this disclosure, smaller ocular abnormalities may be undetected. More specifically, because tiling of a retinal image could result in an insufficient extent of an ocular abnormality remaining in each tile image, the trained detection model may not determine the ocular abnormality as a detected object. As an example, a small hemorrhage split between two tile images may be undetected because that small hemorrhage does not appear as an object to the trained detection model.

Further, tiling a retinal image also may result in the trained detection model being able to identify an object, but the wrong subtype of object. For example, the trained detection model may be unable to identify an ocular abnormality corresponding to an optic nerve because a normal portion of the optic nerve may be present in a tile image an abnormal portion of the optic nerve may be present in another tile image. Thus, in some cases, tiling might yield a misclassification of an object. Assessment of the optic nerve is important because a gradable optic nerve may be a requirement for a gradable set, according to an extant retinal distance-screening program. Also, establishing the actual optic nerve size can be used for further assessments. Proper assessment of the optic nerve can permit the detection protocol, via a trained detection model (e.g., detection model 349 (FIG. 3)), to detect potentially blinding causes of vision loss other than diabetic eye disease (such as glaucoma, papilledema, etc.).

Without intending to be bound by type of detection protocol, in order to the address issues of misclassification and missed detection, the detection stage 130 can include a detection sequence of two or more detection events based on a single image set. In a first detection event, the trained detection model can be applied to an image set. In a second detection event, the image set may be operated upon in order to generate tile images that are offset by a defined number of pixels (e.g., 20 pixels, 30 pixels, or 50 pixels). For example, a 300×300 pixel retinal image may have each one of its constituting 100×100 pixel tile displaced by 50 pixels along a translation direction (e.g., from the left). Although implementation of such a detection sequence may incur additional processing time relative to a detection protocol having a single detection event, a detection protocol in accordance with this disclosure need not run in real time (e.g., it is permitted to run slower than 30 frames per second). Additionally, the added processing time may be offset by the reduction of misclassification and missed detection of objects within an image set.

In the operating environment 300 shown in FIG. 3, the analysis module 344 can include a post-processing component 350 that can generate an offset image set. Each retinal image in the offset image set is partitioned into multiple offset tile images. Each one of the offset tile images contains pixels encompassed by a bounding box resulting from translating, by a defined translation vector, a source bounding box defining a tile image of a retinal image in the image set received by the analysis module 344. More specifically, the analysis module 344 can obtain a retinal image in the image set, and can partition each retinal image in the image set into tile images. In each retinal image, the tile images form a two-dimensional array having a particular number of tile images (e.g., 3×3=9 tile images). The post-processing component 350 can then generate a second image set using the image set. To that end, the post-processing component 350 can generate each retinal image in the second image set by translating the bounding boxes of respective tile images by a defined translation vector, and by selecting pixels within the translated bounding boxes to from offset tile images that from an offset retinal image. Because of application of the defined translation vector, the post-processing component 350 can apply padding in order to generate an offset image having same size as an originating retina image. Padding includes configuring pixels within an offset bounding box to have a defined color (e.g., blue pixels, grey pixels) in order to complete a partial tile image having undefined pixels. A 50% offset in a single direction (horizontally, for example) yields satisfactory results. The analysis module 344 can then implement a detection event using the second image set.

It is noted that even with the application of an offset as is described herein, objects that are split between tile images prior to the application of the offset remain split between the tile images after the application of the offset. As such, a detection protocol can leverage an anticipated shape and/or anticipated size of an object to improve detection accuracy. An example of the application of anticipated shape cam be a spheroidal object split essentially evenly between two tile images, with the resultant portion of the spheroidal object no longer having a 1:1 height/width ratio but rather a 1:2 height/width ratio. Because an optic nerve is an object having a generally circular shape, it could be assumed that any optic nerve with a ratio greater than 9:5 or less than 5:9, for example, is a cropped optical nerve. Additionally, it is uncommon to see specific types of ocular abnormalities (e.g., intraretinal hemorrhages, cotton-wool spots, or drusen) within fundus photos with such irregularly rectangular shapes. Thus, it is more likely that such irregularly shaped objects represented an artifact than an actual object of interest.

Accordingly, detected objects having irregular rectangular shapes can be removed from a group of detected objects. As a result detection accuracy can be improved because of a lesser incidence of artifacts in such a group. In some cases, the post-processing component 350 can perform geometrical analysis of each object within the group of detected objects. Based on such analysis, the post-processing component 350 can remove one or multiple objects deemed to have an irregular geometry. The geometrical analysis can include edge detection, where the structure of edges of an object can be determined. Based on such a structure, such as number of edges and distribution of orientation of the edges, the post-processing component 350 can remove the object from the group or can maintain the object in the group.

In addition to using anticipated object shape, anticipated object size also can be utilized in the detection protocol in order to correct for misclassifications. In ophthalmology, optic nerve size (or "disc diameter") can often be utilized to describe fundus findings and is on average approximately 1.5 mm in size. Therefore, the detection protocol can use the optic nerve as a reference size. The size of the optic nerve (in pixels, for example) can be determined by determining a weighted average of all sizes of respective optic nerves identified within an entire image set. In the weighted average, each size can be weighted based on confidence score, where the confidence score was at least equal to a threshold score. For example, the threshold score can be 0.4. A particular threshold score can be determined using heuristics. For example, a baseline value can be selected and then iteratively modified until a satisfactory number of false positives is observed. Such a weighted average may be referred to as "average optic nerve size." Any hemorrhage objects larger than three times the area of the "average optic nerve size" and any optic nerves smaller than one third of the "average optic nerve size" can be identified as an artifact or partial nerves. Accordingly, the detection protocol can remove objects so identified. Although a single hemorrhage having a size greater than three times the "average optic nerve size" may exist in a retinal photo, such an ocular abnormality may not be an isolated finding. In other words, presence of such a large hemorrhage would be accompanied by other fundus abnormalities. Accordingly, it is unlikely that the detection protocol would mistake any abnormal retinal images as normal by relying on anticipated shape and/or anticipated size.

In the operating environment 300 shown in FIG. 3, the post-processing component 350 can perform the analysis that applies anticipated shape and/or size to detected ocular objects, as is described herein.

Despite of the removal of dust and similar artifacts, a large number of artifacts (e.g., tens of artifacts, for example) can be detected within an image set by a trained detection model (e.g., detection model 349 (FIG. 3)) in the detection stage 130. This results in a large number of hemorrhages and exudates being detected where in fact none existed. To discern between an artifact and an actual ocular abnormality, detected object in a retinal image can be contrasted with detected objects in another retinal image within the image set.

Accordingly, as part of the detection stage 130, objects detected in an image set can be analyzed across the image set. In the operating environment 300 (FIG. 3), the post-processing component 350 can analyze the detected objects across the image set. A resultant list of objects (minimum threshold score set to 0.2, for example) can be combined so as to form a list of objects (and their pixel location coordinates) for each retinal image in the image set, and a list of objects (and their pixel location coordinates) for each image set. The analysis module 344, via the post-processing component 350, for example, can remove any objects that have been detected as intraretinal hemorrhage, dust, cotton-wool spot, or drusen and are positioned in essentially the same absolute location within various photos within an image set. For purposes of illustration, an absolute location can be considered to be essentially the same across the image set when the absolute location remains within a threshold number of pixels (e.g., 5 pixels or 10 pixels) from image to image across the image set. Such a removal operation is justified by the observation that artifacts (such as dust and smudges on the camera) have the same absolute position in the photos of an image set, whereas actual abnormalities have the same relative position. In other words, rather than being germane to the eye being imaged, artifacts pertain to the image itself and how the image has been acquired.

Figure 4:
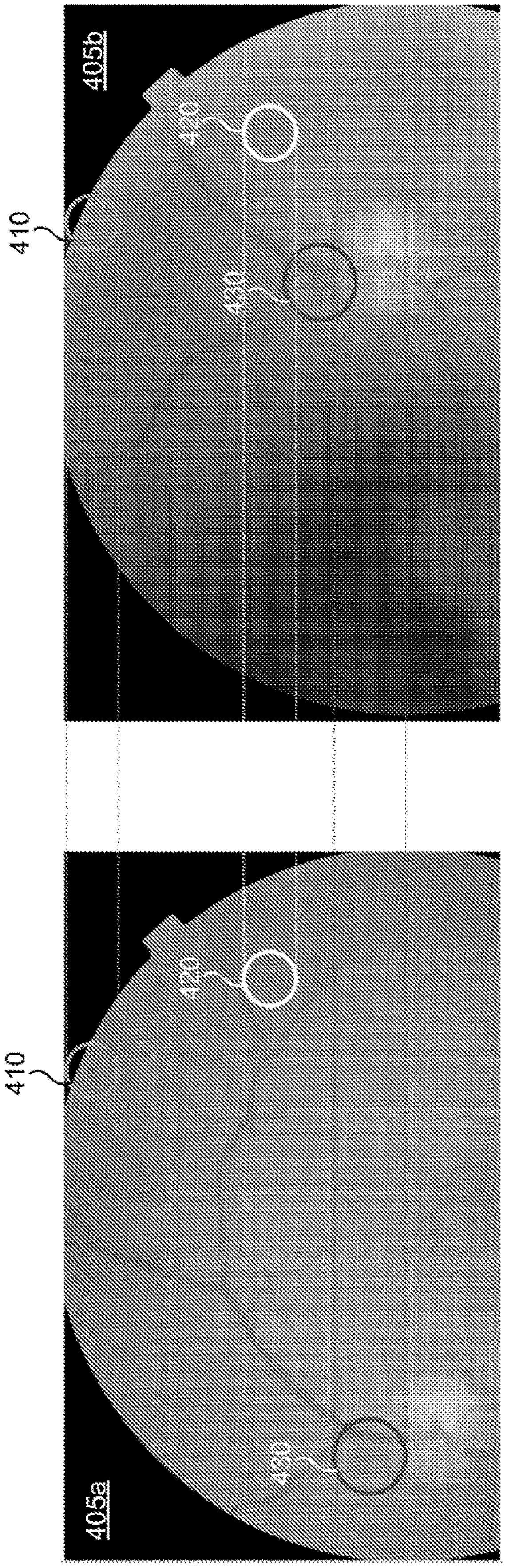
FIG. 4 presents two retinal images of same eye.

Simply as an illustration, FIG. 4 presents two retinal images of same eye that illustrate the use of absolute position and relative position to evaluate objects within the images, in accordance with one or more embodiments of this disclosure. In this case, three reddish small circles were identified in two photos of the same eye. The object enclosed by circle 410 in green and the object enclosed by circle 420 in yellow are deemed to be artifacts because those objects have the same absolute position within the photo (they are seen to line up vertically using the dashed lines). That is, objects within circle 410 and circle 420 are not germane to the eye being imaged, but instead those objects pertain to the image itself and how the image has been acquired. In contrast, the object enclosed by circle 430 in blue has the same position relative to a white/pinkish object (the optic nerve) but has a higher absolute location in photo **405*a* relative to the photo 405*b***, suggesting that this is a real object (a hemorrhage, for example).

After the detection stage 130 (FIG. 1), an evaluation stage 140 can be performed in order to determine whether retinopathy in an image set is present. In the evaluation stage 140, different types of ocular abnormalities (caused by diabetes, for example) can be assigned different weights. Based on the respective confidence scores of the ocular abnormalities and the number of a particular type of ocular abnormality, retinopathy can be deemed present in a particular retinal image. For example, a single instance of a high confidence score hemorrhage, a high confidence score exudate, or a high confidence score cotton wool spot in a retinal image results in that image being deemed retinopathy. As another example, retinopathy can be deemed present, with lower confidence, in cases where a single instance of lower confidence score hemorrhage is present. As yet another example, for ocular abnormalities having lower confidence scores, multiple instances (e.g., 3 instances) are required for retinopathy to be deemed present in the retinal image. In some cases, retinopathy can be deemed present where both a single instance of a higher confidence score ocular abnormality and multiple lower confidence score abnormalities are present in a retinal image. High confidence scores can be greater than about 0.4, for example. Lower confidence scores range from about 0.2 to less than about 0.4, for example. In the operating environment 300 shown in FIG. 3, the evaluation module 352 can analyze the confidence scores of respective ocular abnormalities present in a retinal image.

Additionally, ocular abnormalities detected in different retinal images within an image set can be used to affect the ocular abnormalities detected in another retinal image within the image set. For example, the evaluation module 352 can determine that one retinal image within an image set has ambiguous ocular abnormalities and the other retinal images within the image set are all normal. In response, the evaluation module 352 can then update the ambiguous ocular abnormalities to retinopathy. Updating the ambiguous ocular abnormalities to retinopathy can include, for example, generating an attribute identifying a retinal image and/or an image set as depicting retinopathy. The evaluation module 352 can augment the retinal image or the image set, or both, with such an attribute, and can then retain the augmented retinal image and/or augmented image set within data storage 370, for example. As is shown in FIG. 3, the data storage 370 can be functionally coupled to the server device 340 via a communication architecture 380 (e.g., one more wireline network(s) and/or wireless network(s)). In some embodiments, the communication architecture 380 can be included in the networks 330. The server device 340 (via the evaluation module 352, for example) can retain the augmented retinal image or the augmented image set in the data storage 370 by means of the communication architecture 380.

Likewise, the evaluation module 352 can update ambiguous ocular abnormalities to non-retinopathy if retinopathy was not found in other retinal images within the same image set. Updating the ambiguous ocular abnormalities to non-retinopathy can include, for example, generating an attribute identifying a retinal image and/or an image set as depicting normal retina. The evaluation module 352 can augment the retinal image or the image set, or both, with such an attribute, and can then retain the augmented retinal image and/or augmented image set within data storage 370, for example. The server device 340 (via the evaluation module 352, for example) can retain the augmented retinal image or the augmented image set in the data storage 370 by means of the communication architecture 380.

A client device 390 can access (e.g., query or otherwise read) the data storage 380 to obtain an augmented image set. To that end, the client device 390 can execute a software application (not depicted in FIG. 3). Execution of the software application can cause presentation of the augmented image set at a display device (not depicted in FIG. 3) integrated into the client device or functionally coupled thereto. The client device 390 can be accessed and operated by a reviewer agent (such as an optometrist). In some example scenarios, instead of relying on the communication architecture 380, the client device 390 can access the data storage 380 via one or more networks of the networks 330.

It is noted that disclosure is not limited to implementations at the server device 340. In some embodiments, a computing apparatus at the acquisition site 304 can implement the various functionalities described herein. That computing apparatus can include the DICOM receiver module 342, the analysis module 344, the evaluation module 352, and the memory 360. In addition, or in other embodiments, the client device 390 can implement the functionalities described herein. To that end, the client device 390 can include the analysis module 344 and the evaluation module 352, and, in some cases, the DICOM receiver module 342 and the memory 360. The client device 390 can be located at the site of the image review by an optometrist. In some configurations, the client device 390 can include a client application that can execute the analysis module 344 and/or the evaluation module 352 in accordance with aspects described herein. In other configurations, the client application can execute the analysis module 344 and/or the evaluation module 352 from the server device 340. The client device 390 can obtain image sets from local cache directory to perform the analysis described herein. The set of images can be downloaded from the service device 340 and/or data storage 370, as part of routine human-based image review. Based on performing the analysis described herein, the client device 390 can complement or supplement the human-based image review, and also can automatically records various aspects of the human-based image review, such as reporting and diagnosis recordation. The client application can permit receiving input data indicative of confirmation of results of the machine-learning analysis described herein.

Figure 5:
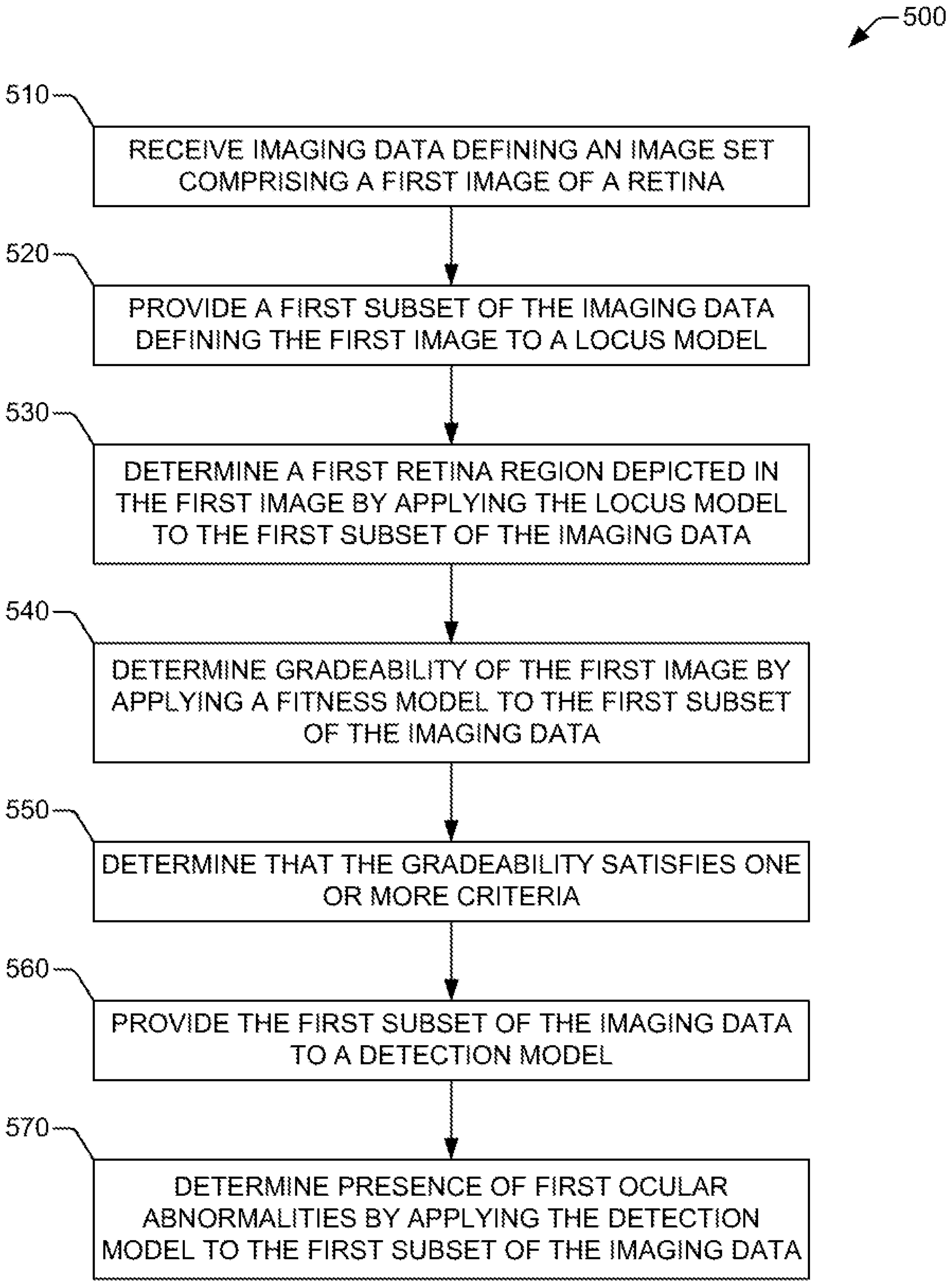
FIG. 5 illustrates an example of a method for detecting ocular abnormalities, in accordance with one or more embodiments of the disclosure.

FIG. 5 illustrates an example of a method 500 for detecting ocular abnormalities, in accordance with one or more embodiments of the disclosure. A computing device or a system of computing devices may implement the example method 500 in its entirety or in part. To that end, each one of the computing devices includes computing resources that may implement at least one of the blocks included in the example method 500. The computing resources can include, for example, central processing units (CPUs), graphics processing units (GPUs), tensor processing units (TPUs), memory, disk space, incoming bandwidth, and/or outgoing bandwidth, interface(s) (such as I/O interfaces or APIs, or both); controller devices(s); power supplies; a combination of the foregoing; and/or similar resources. The computing resources also can include, for example, programming interface(s); an operating system; software for configuration and/or control of a virtualized environment; firmware; and similar resources.

The computing device or the system of computing devices may host the analysis module 344 (FIG. 3), amongst other software modules. In some cases, the computing device can implement the example method 500 by executing one or multiple instances of the analysis module 344. While the example method 500 is described as being implemented by the computing device, the disclosure is not limited in that respect and, in some configurations, the system of computing devices can implemented the example method 500. The computing device can embody the server device 340 (FIG. 3), for example.

At block 510, the computing device can receive imaging data defining an image set. As is described herein, the image set comprises multiple retinal images, including a first image of a retina. The image set can be acquired at an acquisition site (e.g., site 304) that is located at a distance from a campus where the computing system is located.

At block 520, the computing device can provide a first subset of the imaging data defining the first image of the retinal to a locus model. As is described herein, the locus model is a machine-learning model that has been configured to determine a retina region that is depicted in a particular image. Configuring the locus model can include training the locus model to solve a multi-task classification that designates a retinal image as depicting one of multiple regions (e.g., macula, superior region, or nasal region).

At block 530, the computing device can determine a first retina region depicted in the first image by applying the locus model to the first subset of the imaging data. The first region can be the macula region, superior region, or nasal region.

At block 540, the computing system can determine gradeability of the first image by applying a fitness model corresponding to the first retina region. The fitness model can be one of multiple fitness models, each configured to assess gradeability of a retinal image depicting a particular region of retina. Thus, fitness model can correspond to the macula region, the superior region, or the nasal region.

At block 550, the computing system can determine that the gradeability satisfies one or more criteria. Accordingly, the first image of the retina can be deemed gradeable and, thus, adequate for further analysis.

At block 560, the computing system can provide the first subset of the imaging data to a detection model. As is described herein, the detection model is a machine-learning model that has been configured to determine presence of multiple ocular abnormalities within a particular retinal image.

At block 570, the computing system can determine presence of first ocular abnormalities by applying the detection model to the first subset of the imaging data. Applying the detection model to the first subset of the imaging data can yield a first confidence score for the first one of the multiple ocular abnormalities and a second confidence score for a second one of the multiple ocular abnormalities. The first confidence score quantifies likelihood that the first one of the multiple ocular abnormalities is a ground-truth observation, and the second confidence score quantifies likelihood that the second one of the multiple ocular abnormalities is another ground-truth observation.

The example method 500 can be implemented for each retinal image present in the image set. As a result, a collection of multiple ocular abnormalities can be detected can be identified. Such a collection can be evaluated in order to draw a conclusion of presence or absence of retinopathy within the image set.

Figure 6:
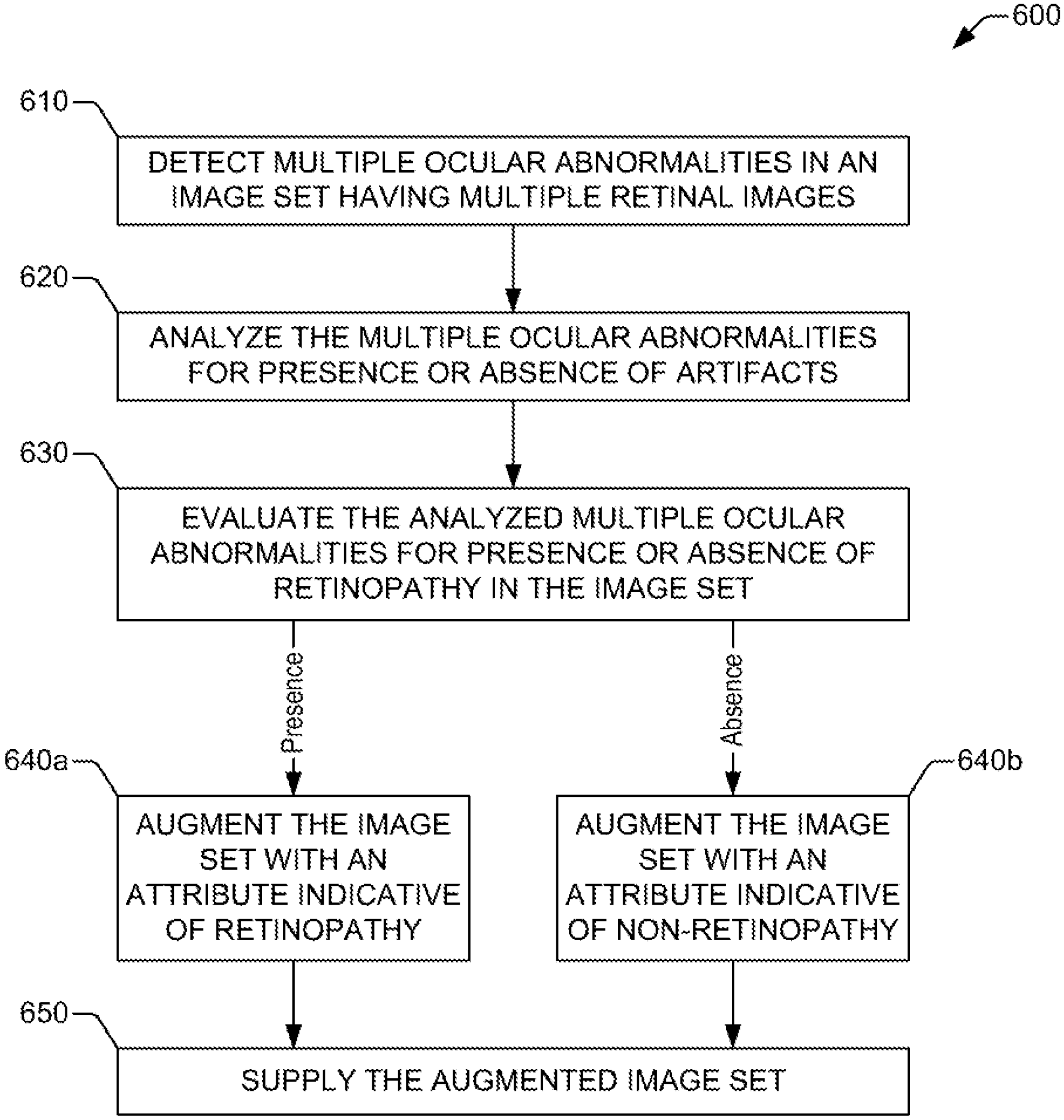
FIG. 6 illustrates an example of a method for evaluating ocular abnormalities detected in an image set, in accordance with one or more embodiments of the disclosure.

FIG. 6 illustrates an example of a method 600 for evaluating ocular abnormalities detected in an image set, in accordance with one or more embodiments of the disclosure. The computing device or the system of computing devices that implements the example method 500 also can implement the example method 600 in its entirety or in part. As such, the computing device or system of computing devices can host the evaluation module 352, for example. While the example method 600 is described as being implemented by the computing device, the disclosure is not limited in that respect and, in some configurations, the system of computing devices can implement the example method 600. The computing device can embody the server device 340 (FIG. 3), for example.

At block 610, the computing device can detect multiple ocular abnormalities in an image set having multiple retinal images. To that end, the computing device can perform the example method 500 for each retinal image in the image set. As mentioned, the image set can include at least six retinal images.

At block 620, the computing device can analyze the multiple ocular abnormalities for presence or absence of artifacts. As is described herein, an ocular abnormality that is detected in a retinal image may indeed be an artifact, such as particulate matter or another type of feature that is not germane to the retina being evaluated. Analyzing the multiple ocular abnormalities in such a fashion can include, for example, comparing position of an ocular abnormality in a first retinal image and position of another ocular abnormality in a second retinal image. As part of such a comparison, the analysis can include determining that a first ocular abnormality in the first retinal image and a second ocular abnormality in the second retinal image have a same position vector in a reference coordinate system defined in each one the first and second retinal images. See FIG. 4, for example. Based on such determination, the computing system can update a record of the multiple ocular abnormalities to exclude the first ocular abnormality and the second ocular abnormality.

At block 630, the computing device can evaluate the analyzed multiple ocular abnormalities for present or absence of retinopathy in the image set. In the absence of artifacts, the analyzed multiple ocular abnormalities are the same as the detected multiple ocular abnormalities. In the presence of artifacts, the computing device can remove those artifacts from a listing of detected objects (and locations thereof) and can then update the detected multiple ocular abnormalities accordingly. As a result, the analyzed multiple ocular abnormalities are fewer than the detected multiple ocular abnormalities.

In some cases, evaluating the analyzed multiple ocular abnormalities can include determining that the updated record of the multiple ocular abnormalities includes a particular one of the multiple ocular abnormalities having a confidence score that exceeds a threshold value. Based on such a determination, the computing system can determine that retinopathy is present in the image set.

In other cases, evaluating the analyzed multiple ocular abnormalities can include determining that the updated record of the multiple ocular abnormalities includes a defined number of particular ocular abnormalities having respective confidence scores less than a threshold value. Based on such a determination, the computing system can determine that retinopathy is absent from the image set.

Presence of retinopathy can direct the flow of the example method 600 to block 640*a*, where the computing device can augment the image set with attribute indicative of retinopathy. The attribute can include data identifying the image set as presenting retinopathy. Absence of retinopathy, can direct the flow of the example method 600 to block 640*b*, where the computing device can augment the image set with an attribute indicative of non-retinopathy. The attribute can include data identifying the image set as presenting retinopathy.

Regardless of the type of data included in the attribute, the attribute can serve as metadata that can control the presentation of the image set at a client device operated by a human reviewer. For example, the attribute can cause a client application to cause or otherwise direct a display device to present one or more markings indicating presence of retinopathy. In some cases, multiple markings can be presented, including an image and text. Further, or in another example, the display device can be caused or otherwise directed to present one or more other markings indicating the present of other abnormalities, such as drusen (a hallmark of macular degeneration) and/or abnormal appearing optic nerve (an indicator of glaucoma and other neuropathies). The display device can be integrated into the client device or can be functionally coupled thereto.

At block 650, the computing device can supply the augmented image set. Supplying the image set can include retaining the augmented image set in data storage (e.g., data storage 370 (FIG. 3)), for example.

Figure 7:
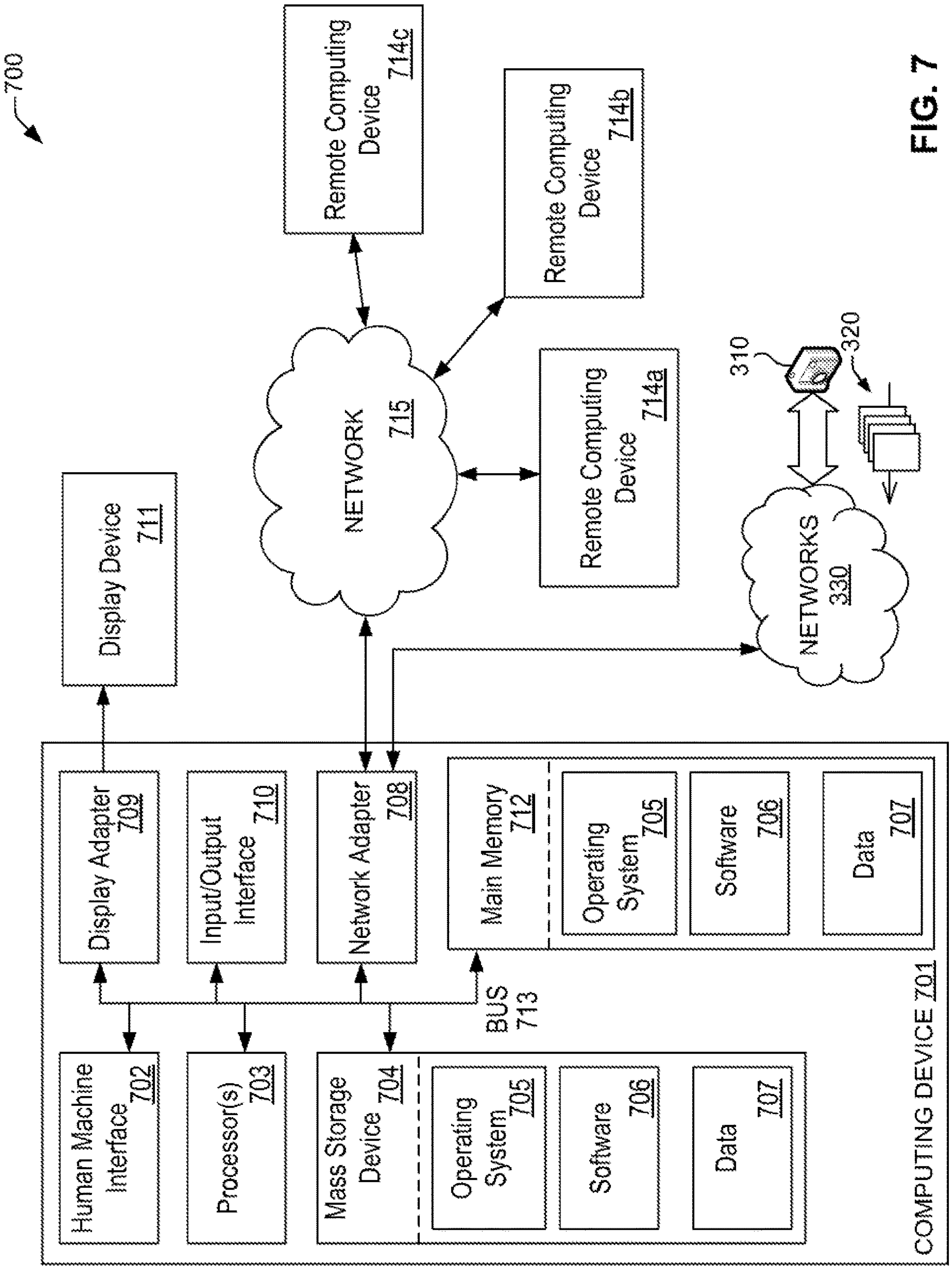
FIG. 7 illustrates an example of computing environment to implement retinal distance-screening using machine learning, in accordance with one or more embodiments of the disclosure.

Retinal distance-screening using machine learning in accordance with aspects described herein can be implemented on the computing environment 700 illustrated in FIG. 7 and described below. The computer-implemented methods and systems disclosed herein may utilize one or more computing devices to perform one or more functions in one or more locations. FIG. 7 is a block diagram depicting an example computing environment 300 for performing the disclosed methods and/or implementing the disclosed systems. The computing environment 700 is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment. The computing environment 700 shown in FIG. 7 may embody at least a portion of the example operating environment 300 (FIG. 3). In other cases, the computing environment 700 also can embody at least a portion of the example operating environment 250 (FIG. 2B). The computing environment 700 may implement the various functionalities described herein in connection with retinal distance-screening using machine learning. For example, one or more of the computing devices shown in the computing environment 700 may comprise the DICOM receiver module 342, the analysis module 344, the data storage 370, and the client device 390 shown in FIG. 3. In addition, or as another example, the computing environment 700 also can include the labeled data repository 254, the training module 270, and the model repository 280.

The computer-implemented methods and systems in accordance with this disclosure may be operational with numerous other general purpose or special purpose computing system environments or configurations. Examples of well-known computing systems, environments, and/or configurations that may be suitable for use with the systems and methods comprise, but are not limited to, personal computers, server computers, laptop devices, and multiprocessor systems. Additional examples comprise set-top boxes, programmable consumer electronics, network PCs, minicomputers, mainframe computers, distributed computing environments that comprise any of the above systems or devices, and the like.

The processing of the disclosed computer-implemented methods and systems may be performed by software components. The disclosed systems and computer-implemented methods may be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods may also be practiced in grid-based and distributed computing environments where tasks are performed by remote processing devices that are linked through a communications network. In a distributed computing environment, program modules may be located in both local and remote computer storage media including memory storage devices.

Further, the systems and computer-implemented methods disclosed herein may be implemented via a general-purpose computing device in the form of a computing device 701. The components of the computing device 701 may comprise one or more processors 703, a system memory 712, and a system bus 713 that couples various system components including the one or more processors 703 to the system memory 712. The system may utilize parallel computing.

The system bus 713 represents one or more of several possible types of bus structures, including a memory bus or memory controller, a peripheral bus, an accelerated graphics port, or local bus using any of a variety of bus architectures. The system bus 713, and all buses specified in this description may also be implemented over a wired or wireless network connection and each of the subsystems, including the one or more processors 703, a mass storage device 704, an operating system 705, software 706, data 707, a network adapter 708, the system memory 712, an Input/Output interface 710, a display adapter 709, a display device 711, and a human-machine interface 702, may be contained within one or more remote computing devices 714*a,b,c* at physically separate locations, connected through buses of this form, in effect implementing a fully distributed system.

The computing device 701 typically comprises a variety of computer-readable media. Exemplary readable media may be any available media that is accessible by the computing device 701 and comprises, for example, both volatile and non-volatile media, removable and non-removable media. The main memory 712 comprises computer readable media in the form of volatile memory, such as random access memory (RAM), and/or non-volatile memory, such as read only memory (ROM). The main memory 712 typically contains data such as the data 707 and/or program modules such as the operating system 305 and the software 306 that are immediately accessible to and/or are presently operated on by the one or more processors 303. For example, the software 706 may include the analysis module 344 (FIG. 3) and the evaluation module 352. The operating system 705 may be embodied in one of Windows operating system, Unix, or Linux, for example. In addition, or in some cases, the software 706 can include the training module 270.

In another aspect, the computing device 701 may also comprise other removable/non-removable, volatile/non-volatile computer storage media. For example, FIG. 7 illustrates the mass storage device 704 which may provide non-volatile storage of computer code, computer readable instructions, data structures, program modules, and other data for the computing device 701. For example and not meant to be limiting, the mass storage device 704 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 704, including by way of example, the operating system 705 and the software 706. Each of the operating system 705 and the software 706 (or some combination thereof) may comprise elements of the programming and the software 706. The data 707 may also be stored on the mass storage device 704. The data 707 may be stored in any of one or more databases known in the art. Examples of such databases comprise, DB2®, Microsoft® Access, Microsoft® SQL Server, Oracle®, mySQL, PostgreSQL, SQLite, and the like. The databases may be centralized or distributed across multiple systems. It is noted that SQLite and other of such databases can be used with various forms of DICOM received modules (e.g., DICOM receiver module 342), such as open-source DICOM receiver modules.

In another aspect, the user may enter commands and information into the computing device 701 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices may be connected to the one or more processors 703 via the human-machine interface 702 that is coupled to the system bus 713, but may be connected by other interface and bus structures, such as a parallel port, game port, an IEEE 1394 Port (also known as a Firewire port), a serial port, or a universal serial bus (USB).

In yet another aspect, the display device 711 may also be connected to the system bus 713 via an interface, such as the display adapter 709. It is contemplated that the computing device 701 may have more than one display adapter 709 and the computing device 701 may have more than one display device 711. For example, the display device 711 may be a monitor, an LCD (Liquid Crystal Display), or a projector. In addition to the display device 711, other output peripheral devices may comprise components such as speakers (not shown) and a printer (not shown) which may be connected to the computing device 701 via the Input/Output Interface 710. Any operation and/or result of the methods may be output in any form to an output device. Such output may be any form of visual representation, including, but not limited to, textual, graphical, animation, audio, tactile, and the like. The display device 711 and computing device 701 may be part of one device, or separate devices.

The computing device 701 may operate in a networked environment using logical connections to one or more remote computing devices 714*a,b,c*. For example, a remote computing device may be a personal computer, portable computer, smartphone, a server device, a router device, a network computer, a peer device or other common network node, and so on. Logical connections between the computing device 301 and a remote computing device 714*a,b,c* may be made via a network 715, such as a LAN and/or a general WAN. Such network connections may be through the network adapter 708. The network adapter 708 may be implemented in both wired and wireless environments. In some cases, one of the remote computing devices 714*a,b,c* can embody the client device 390 (FIG. 3). Accordingly, the network 715 may embody, for example, the communication architecture 380 (FIG. 3).

For purposes of illustration, application programs and other executable program components such as the operating system 705 are illustrated herein as discrete blocks, although it is recognized that such programs and components reside at various times in different storage components of the computing device 701, and are executed by the one or more processors 703 of the computer. An implementation of the software 706 may be stored on or transmitted across some form of computer-readable media. Any of the disclosed methods may be performed by computer readable instructions embodied on computer-readable media. Computer-readable media may be any available media that may be accessed by a computer. By way of example and not meant to be limiting, computer-readable media may comprise "computer storage media" and "communications media." "Computer storage media" comprise volatile and non-volatile, removable and non-removable media implemented in any methods or technology for storage of information such as computer-readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by a computer.

Figure 8:
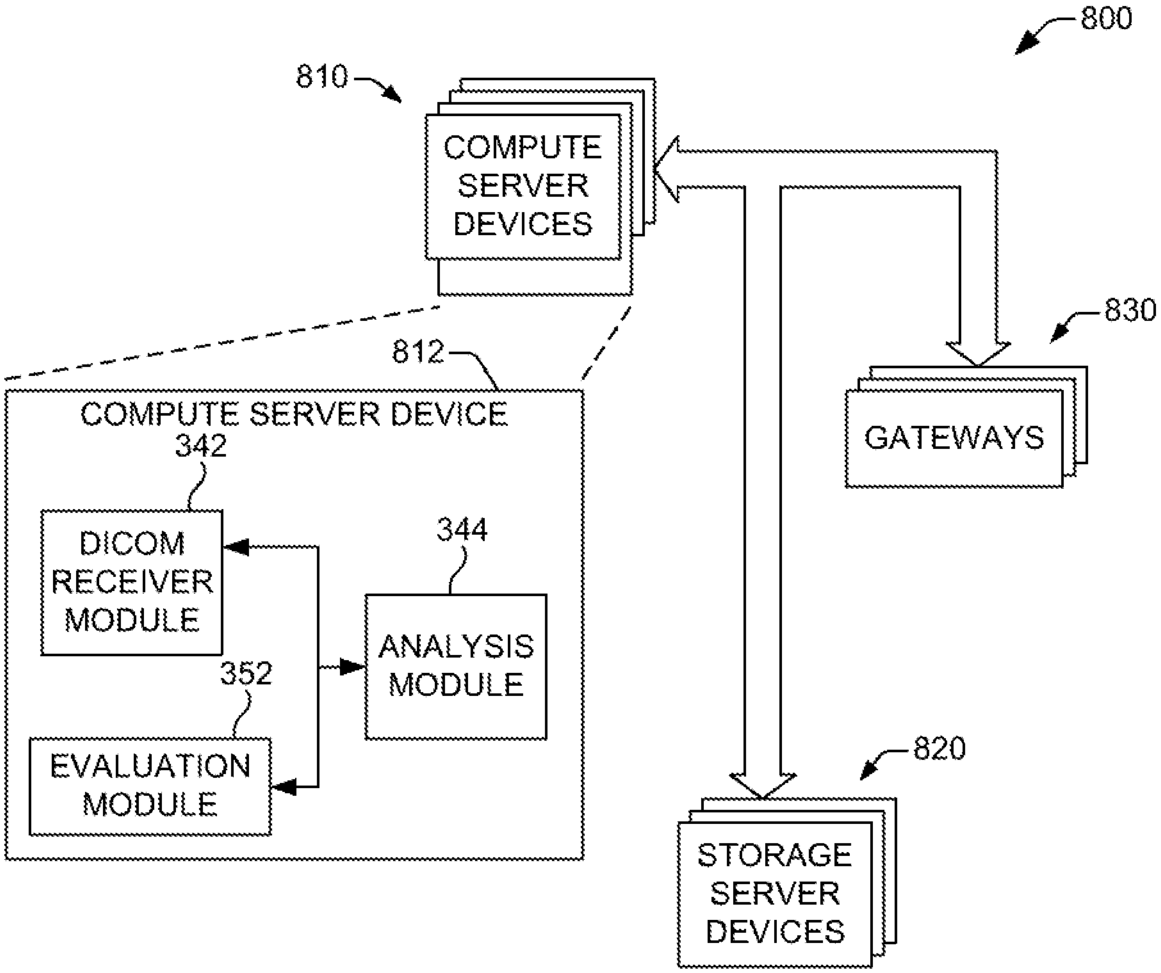
FIG. 8 illustrates another example of a computing environment to implement retinal distance-screening using machine learning, in accordance with one or more embodiments of this disclosure.

FIG. 8 is a schematic block diagram of an example of a computing environment 800 to implement retinal distance-screening using machine learning, in accordance with one or more embodiments of this disclosure. The computing environment 800 that can embody, or can include, a portion of the computing environment 300 (FIG. 3). Accordingly, the example computing environment 300 can provide the functionality described herein in connection with the retinal distance-screening implemented in the computing environment 300 and described herein.

The example computing system 800 includes two types of server devices: Compute server devices 810 and storage server devices 820. A subset of the compute server devices 810, individually or collectively, can host the various modules that permit implementing retinal distance-screening using machine-learning in accordance with aspects described herein. Thus, such a subset of compute server device 810 can operate in accordance with functionality described herein in connection with retinal distance-screening using machine learning. For the sake of illustrations a particular compute server device 812 within such a subset is schematically depicted as hosting such modules—e.g., DICOM received module 342, the analysis module 344, and the evaluation module 352. Similar to the computing device 601 (FIG. 6A), the architecture of the compute server device 662 comprises one or more processors, one or more memory devices, and a bus architecture that functionally couples such components. The modules hosted by the compute server device 662 can be stored in at least one of the memory device(s). At least the subset of the compute server devices 810 can be functionally coupled to one or many of the storage server devices 820. That coupling can be direct or can be mediated by at least one of gateway devices 830. The storage server devices 820 include data and/or metadata that can be used to implement the functionality described herein in connection with the retinal distance-screening using machine learning. Some or all of the storage server devices 820 can embody, or can constitute, the memory 360 (FIG. 3).

Each one of the gateway devices 830 can include one or many processors functionally coupled to one or many memory devices that can retain application programming interfaces (APIs) and/or other types of program code for access to the compute server devices 810 and storage server devices 820. Such access can be programmatic, via an appropriate function call, for example. The subset of the compute server devices 810 that host the DICOM receiver module 342, the analysis module 344, and the evaluation module 352 also can use API(s) supplied by the gateway devices 830 in order to provide results of implementing the functionalities described herein in connection with retinal distance-screening using machine-learning in accordance with aspects described herein.

Figure 9:
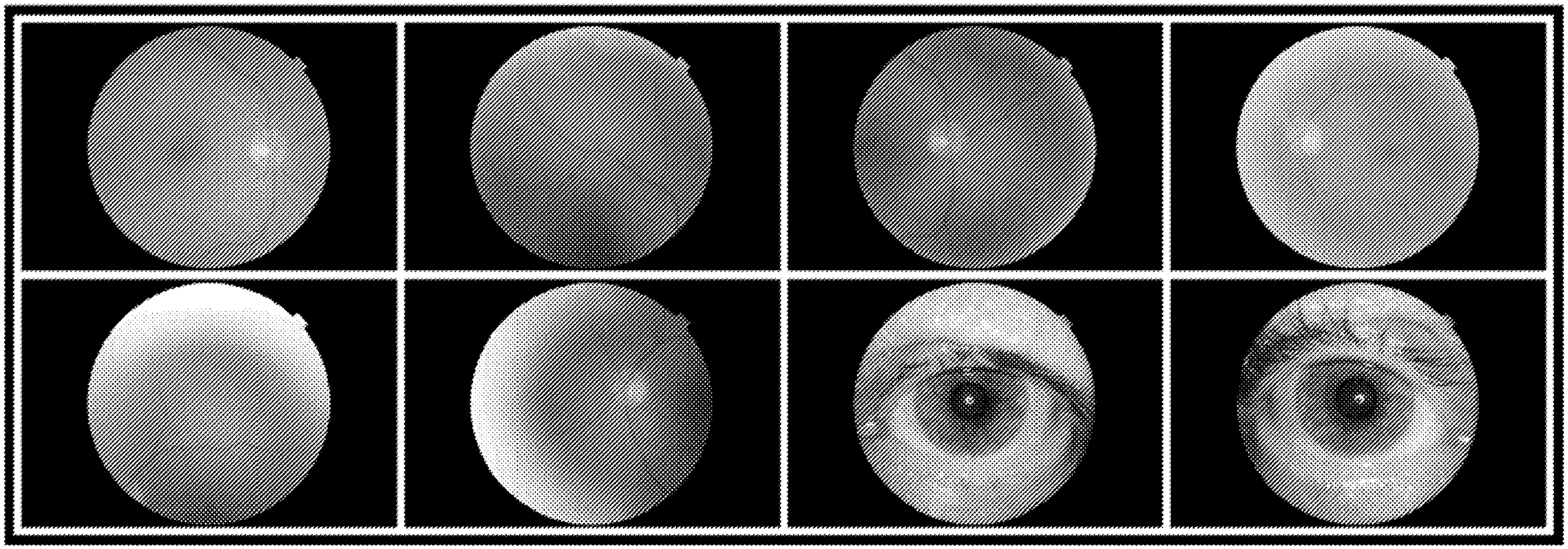
FIG. 9 illustrates examples of input that an analysis module can receive and output from the analysis module, in accordance with one or more embodiments of this disclosure.

FIG. 9 illustrates examples of input that the analysis module 344 can receive and output from the analysis module 344, in accordance with one or more embodiments of this disclosure. A Veteran's image set that has been obtained during a retinal distance-screening (or teleretinal screening) can be analyzed by the analysis module 344. The image set includes at least one gradable image for each of three desired or otherwise required regions per eye (Panel A in FIG. 9). Results generated by the analysis module 344 in combination with the evaluation module 360, in some cases, indicate that the subject requires additional review (see Panel B in FIG. 9).

Figure 10:
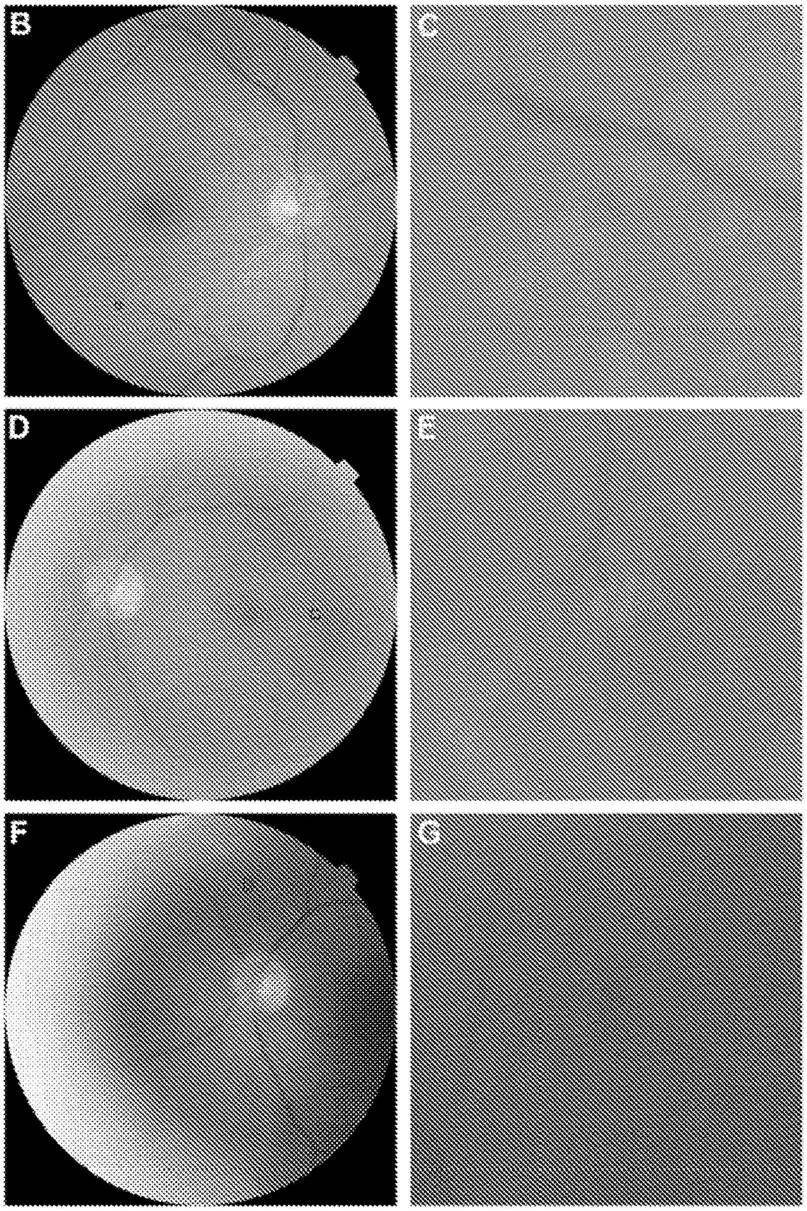
FIG. 10 illustrates an example of a detailed analysis report from the same Veteran referred to in FIG. 9.

FIG. 10 illustrates an example of a detailed analysis report from the same Veteran referred to in FIG. 9, in accordance with one or more embodiments of this disclosure. Panel (A): Each row corresponds to each image in the image set from Panel A in FIG. 9 and includes output data from the machine-learning analysis that can be performed in accordance with aspects described herein. For each image within the image set, the analysis module 344 can cause the client device 390 to display both the original image with a superimposed blue box showing the most likely positive finding (Panels B, D, F) and corresponding magnified views to the right (Panels C, E, G).

Figure 11:
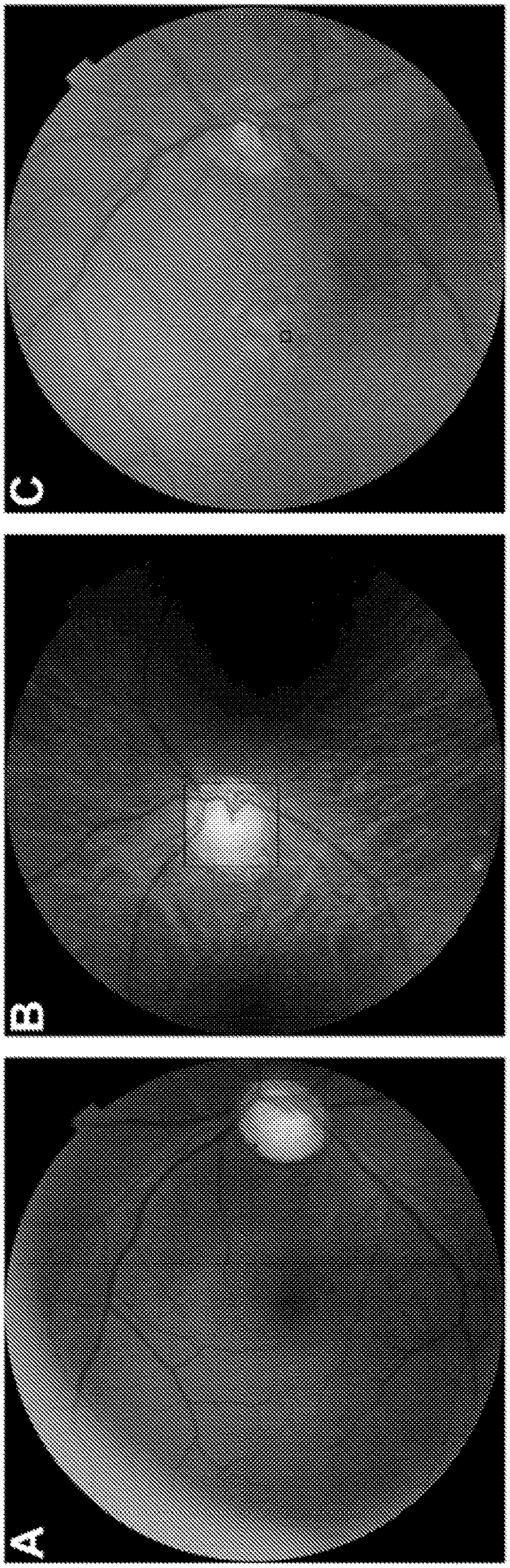
FIG. 11 illustrates detection of ocular disease based on the machine-learning analysis that can be performed in accordance with aspects described herein.

FIG. 11 illustrates detection of ocular disease based on the machine-learning analysis that can be performed in accordance with aspects described herein. The analysis module 344 and the evaluation module 352 can detect, using the machine learning models and evaluation techniques described herein, both nerves suspicious for glaucoma (Panels A, B) as well as drusen, a feature of age-related macular degeneration (Panel C). The analysis module 344 and the evaluation module 352 can cause the client device 390 to present visual elements that identify or otherwise mark this flagged region with a blue box.

Figure 12:
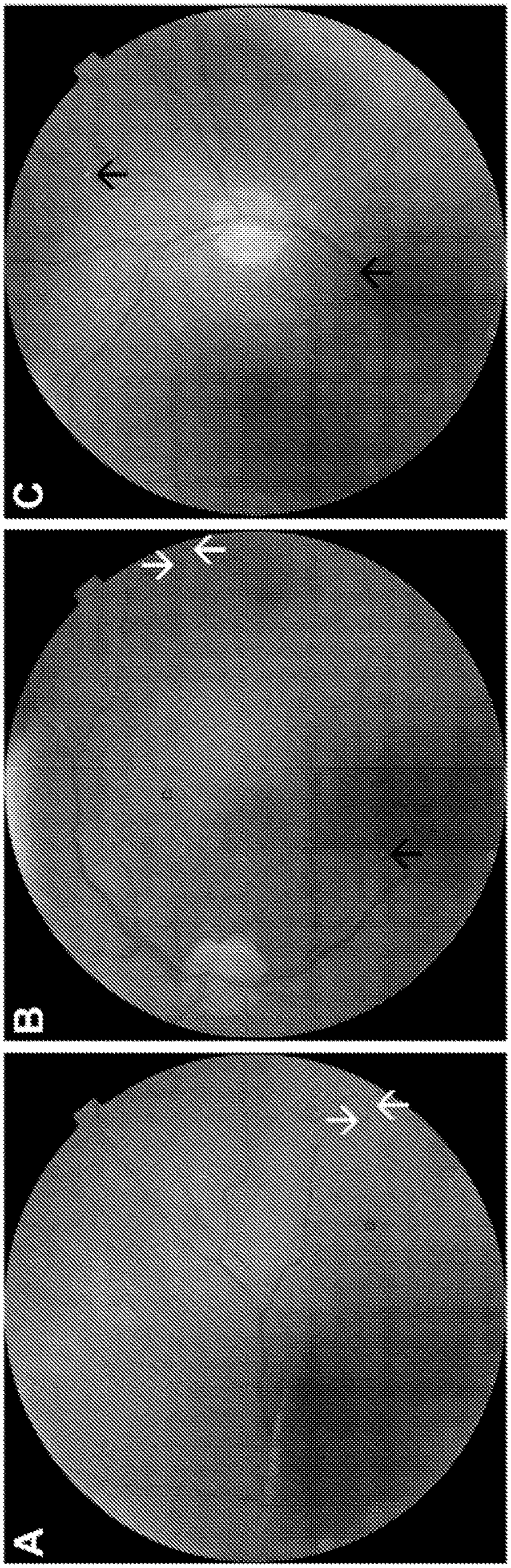
FIG. 12 illustrates an example of results generated by embodiments of this disclosure.

FIG. 12 illustrates an example of results generated by embodiments of this disclosure. Results obtained by applying the machine learning models and evaluation techniques described herein to an image set from a veteran with mild NPDR (nonproliferative diabetic retinopathy) is demonstrated with photos of the left eye shown in Panels A and B and the right eye shown in Panel C. The analysis module 344 and the evaluation module 352 can cause the client device 390 to present visual elements that mark the photos with blue boxes to indicate the most likely positive finding for diabetic retinopathy. Simply for the sake of clarity, all arrows have been manually superimposed to the output of the application of the machine learning models and evaluation techniques described herein. White arrows demonstrate other hemorrhages present. Black arrows indicate hollenhorst plaques.

It is to be understood that the methods and systems described here are not limited to specific operations, processes, components, or structure described, or to the order or particular combination of such operations or components as described. It is also to be understood that the terminology used herein is for the purpose of describing example embodiments only and is not intended to be restrictive or limiting.

As used herein the singular forms "a," "an," and "the" include both singular and plural referents unless the context clearly dictates otherwise. Values expressed as approximations, by use of antecedents such as "about" or "approximately," shall include reasonable variations from the referenced values. If such approximate values are included with ranges, not only are the endpoints considered approximations, the magnitude of the range shall also be considered an approximation. Lists are to be considered exemplary and not restricted or limited to the elements comprising the list or to the order in which the elements have been listed unless the context clearly dictates otherwise.

Throughout the specification and claims of this disclosure, the following words have the meaning that is set forth: "comprise" and variations of the word, such as "comprising" and "comprises," mean including but not limited to, and are not intended to exclude, for example, other additives, components, integers, or operations. "Include" and variations of the word, such as "including" are not intended to mean something that is restricted or limited to what is indicated as being included, or to exclude what is not indicated. "May" means something that is permissive but not restrictive or limiting. "Optional" or "optionally" means something that may or may not be included without changing the result or what is being described. "Prefer" and variations of the word such as "preferred" or "preferably" mean something that is exemplary and more ideal, but not required. "Such as" means something that serves simply as an example.

Operations and components described herein as being used to perform the disclosed methods and construct the disclosed systems are illustrative unless the context clearly dictates otherwise. It is to be understood that when combinations, subsets, interactions, groups, etc. of these operations and components are disclosed, that while specific reference of each various individual and collective combinations and permutation of these may not be explicitly disclosed, each is specifically contemplated and described herein, for all methods and systems. This applies to all aspects of this application including, but not limited to, operations in disclosed methods and/or the components disclosed in the systems. Thus, if there are a variety of additional operations that may be performed or components that may be added, it is understood that each of these additional operations may be performed and components added with any specific embodiment or combination of embodiments of the disclosed systems and methods.

Embodiments of this disclosure may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof, whether internal, networked, or cloud-based.

Embodiments of this disclosure have been described with reference to diagrams, flowcharts, and other illustrations of computer-implemented methods, systems, apparatuses, and computer program products. Each block of the block diagrams and flowchart illustrations, and combinations of blocks in the block diagrams and flowchart illustrations, respectively, may be implemented by processor-accessible instructions. Such instructions may include, for example, computer program instructions (e.g., processor-readable and/or processor-executable instructions). The processor-accessible instructions may be built (e.g., linked and compiled) and retained in processor-executable form in one or multiple memory devices or one or many other processor-accessible non-transitory storage media. These computer program instructions (built or otherwise) may be loaded onto a general-purpose computer, special purpose computer, or other programmable data processing apparatus to produce a machine. The loaded computer program instructions may be accessed and executed by one or multiple processors or other types of processing circuitry. In response to execution, the loaded computer program instructions provide the functionality described in connection with flowchart blocks (individually or in a particular combination) or blocks in block diagrams (individually or in a particular combination). Thus, such instructions which execute on the computer or other programmable data processing apparatus create a means for implementing the functions specified in the flowchart blocks (individually or in a particular combination) or blocks in block diagrams (individually or in a particular combination).

These computer program instructions may also be stored in a computer-readable memory that may direct a computer or other programmable data processing apparatus to function in a particular manner, such that the instructions stored in the computer-readable memory produce an article of manufacture including processor-accessible instruction (e.g., processor-readable instructions and/or processor-executable instructions) to implement the function specified in the flowchart blocks (individually or in a particular combination) or blocks in block diagrams (individually or in a particular combination). The computer program instructions (built or otherwise) may also be loaded onto a computer or other programmable data processing apparatus to cause a series of operations to be performed on the computer or other programmable apparatus to produce a computer-implemented process. The series of operations may be performed in response to execution by one or more processor or other types of processing circuitry. Thus, such instructions that execute on the computer or other programmable apparatus provide operations for implementing the functions specified in the flowchart blocks (individually or in a particular combination) or blocks in block diagrams (individually or in a particular combination).

Accordingly, blocks of the block diagrams and flowchart diagrams support combinations of means for performing the specified functions in connection with such diagrams and/or flowchart illustrations, combinations of operations for performing the specified functions and program instruction means for performing the specified functions. Each block of the block diagrams and flowchart illustrations, and combinations of blocks in the block diagrams and flowchart illustrations, may be implemented by special purpose hardware-based computer systems that perform the specified functions or operations, or combinations of special purpose hardware and computer instructions.

The methods and systems may employ artificial intelligence techniques such as machine learning and iterative learning. Examples of such techniques include, but are not limited to, expert systems, case-based reasoning, Bayesian networks, behavior-based AI, neural networks, fuzzy systems, evolutionary computation (e.g. genetic algorithms), swarm intelligence (e.g. ant algorithms), and hybrid intelligent systems (e.g. expert inference rules generated through a neural network or production rules from statistical learning).

While the computer-implemented methods, apparatuses, devices, and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its operations be performed in a specific order. Accordingly, where a method claim does not actually recite an order to be followed by its operations or it is not otherwise specifically stated in the claims or descriptions that the operations are to be limited to a specific order, it is in no way intended that an order be inferred, in any respect. This holds for any possible non-express basis for interpretation, including: matters of logic with respect to arrangement of operations or operational flow; plain meaning derived from grammatical organization or punctuation; the number or type of embodiments described in the specification.

It will be apparent to those skilled in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method, comprising:

obtaining, by a computing device comprising at least one processor, imaging data associated with a plurality of first retinal images;

generating, based on a first tessellation for each first retinal image of the plurality of first retinal images, a plurality of second retinal images;

generating, based on a second tessellation for each first retinal image of the plurality of first retinal images, a plurality of third retinal images, wherein each second tessellation of the plurality of second tessellations corresponds to a spatially displaced version of each corresponding first tessellation of the plurality of first tessellations; and generating, based on the multiple of third retinal images, a detection model configured to determine a presence of a plurality of ocular abnormalities within retinal image, wherein the detection model outputs a first confidence score for a first ocular abnormality of the plurality of ocular abnormalities and a second confidence score for a second ocular abnormality of the plurality of ocular abnormalities, wherein the first confidence score is associated with a likelihood that the first ocular abnormality is a ground-truth observation and the second confidence score is associated with a likelihood that the second ocular abnormality is another ground-truth observation.

2. The method of claim 1, wherein the plurality of ocular abnormalities comprise one or more of intraretinal hemorrhage, particulate matter, a cotton-wool spot, or drusen.

3. The method of claim 1, wherein obtaining the imaging data comprises:

receiving second imaging data associated with a plurality of images of undilated eyes or dilated eyes, wherein the plurality of images are generated over a first time interval using teleretinal screening; and generating, based on the plurality of images, a machine-learning model configured to identify an image of the plurality of images comprising one of a first retina region, a second retina region, or a third retina region.

4. The method of claim 3, further comprising:

generating a second machine-learning model configured to determine gradeability of a first image of the plurality of images comprising the first retina region;

generating a third machine-learning model configured to determine gradeability of a second image of the plurality of images comprising the second retina region; and generating a fourth machine-learning model configured to determine gradeability of a third image of the plurality of images comprising the third retina region.

5. The method of claim 4, wherein obtaining the imaging data further comprises:

applying the machine-learning model to the imaging data associated with an image of the plurality of images of the undilated eyes or dilated eyes;

determining, based on the application of the machine-learning model to the imaging data associated with the image of the undilated eyes or dilated eyes, that the image of the undilated eyes or dilated eyes comprises a retina region;

determining gradeability of the image of the undilated eyes or dilated eyes, based on an application of one of the second machine-learning model, the third machine-learning model, or the fourth machine-learning model to the imaging data associated with the image of the undilated eyes or dilated eyes;

determining that the gradeability satisfies one or more criteria; and updating the imaging data to include data associated with the image of the undilated eyes.

6. The method of claim 4, wherein the machine-learning model comprises a multi-task classification model, and wherein generating, based on the plurality of images, the machine-learning model comprises training the multi-task classification model using a transfer learning technique.

7. The method of claim 4, wherein the first retina region comprises macula region, the second retina region comprises superior region, and the third retina region comprises nasal region.

8. The method of claim 4, wherein generating the second machine-learning model comprises operating on the first image, wherein operating on the first image comprises at least one of:

applying a reflection operation about a defined plane to the first image, applying a rotation operation about a defined axis to the first image, magnifying by a defined factor the first image, or cropping the first image to exclude defined pixels.

9. The method of claim 4, wherein generating the third machine-learning model comprises operating on the second image, wherein operating on the second image comprises at least one of:

applying a reflection operation about a defined plane to the second image, applying a rotation operation about a defined axis to the second image, magnifying by a defined factor the second image, or cropping the second image to exclude defined pixels.

10. The method of claim 4, wherein generating the fourth machine-learning model comprises operating on the third image, wherein operating on the third image comprises at least one of:

applying a reflection operation about a defined plane to the third image, applying a rotation operation about a defined axis to the third image, magnifying by a defined factor the third image, or cropping the third image to exclude defined pixels.

11. The method of claim 1, further comprising:

receiving second imaging data associated with retinal image;

determining, based on an application of a first machine-learning model to the second imaging data associated with the retinal image, that the retinal image comprises a particular retina region;

determining, based on an application of a second machine-learning model to the second imaging data associated with the retinal image, gradeability of the retinal image;

determining that the gradeability satisfies one or more criteria; and determining, based on an application of the detection model to the second imaging data associated with the retinal image, a presence of an ocular abnormality.

12. The method of claim 11, further comprising:

determining that the ocular abnormality is associated with a confidence score that exceeds a threshold value; and generating an attribute indicating that retinopathy is present in the retinal image.

13. A method, comprising:

receiving, by a computing device comprising at least one processor, imaging data associated with an image set comprising a first retinal image;

providing a first subset of the imaging data associated with the first retinal image to a locus model configured to determine a retina region that is depicted in a retinal image;

determining, based on an application of the locus model to the first subset of the imaging data, a first retina region depicted in the first retinal image;

determining, based on an application of a first fitness model to data indicative of the first retina region, gradeability of the first retinal image;

determining that the gradeability satisfies one or more criteria;

providing the first subset of the imaging data to a detection model configured to determine a presence of a plurality of ocular abnormalities within a retinal image; and determining, based on an application of the detection model to the first subset of the imaging data, a presence of a plurality of ocular abnormalities, wherein the detection model outputs a first confidence score for a first ocular abnormality of the plurality of ocular abnormalities and a second confidence score for a second ocular abnormality of the plurality of ocular abnormalities, wherein the first confidence score is associated with a likelihood that the first ocular abnormality is a ground-truth observation and the second confidence score is associated with a likelihood that the second ocular abnormality is another ground-truth observation.

14. The method of claim 13, wherein the image set further comprises a second retinal image, wherein the method further comprises:

providing a second subset of the imaging data associated with the second retinal image to the locus model;

determining, based on an application of the locus model to the second subset of the imaging data, a second retina region depicted in the second retinal image;

determining, based on an application of a second fitness model to data indicative of the second retina region, gradeability of the second retinal image;

determining that the gradeability satisfies the one or more criteria;

providing the second subset of the imaging data to the detection model; and determining, based on an application of the detection model to the second subset of the imaging data, a presence of a plurality of second ocular abnormalities.

15. The method of claim 14, further comprising:

determining that an ocular abnormality of the plurality of ocular abnormalities and an ocular abnormality of the plurality of second ocular abnormalities have a same position vector in a reference coordinate system; and updating a record of the plurality of ocular abnormalities to exclude the ocular abnormality of the plurality of ocular abnormalities.

16. The method of claim 15, further comprising:

determining that the updated record of the plurality of ocular abnormalities comprises another ocular abnormality of the plurality of ocular abnormalities that is associated with a confidence score that exceeds a threshold value; and generating an attribute indicating that retinopathy is present in the first retinal image.

17. The method of claim 15, further comprising:

determining that the updated record of the plurality of ocular abnormalities comprises data indicative of one or more ocular abnormalities that is associated with corresponding one or more confidence scores less than a threshold value; and generating an attribute indicating that retinopathy is absent in the first retinal image.

18. The method of claim 13, wherein the multiple ocular abnormalities include intraretinal hemorrhage, particulate matter, a cotton-wool spot, or drusen.

19. The method of claim 13, wherein the first retina region comprises one or more of a macula region, a superior region, or a nasal region.

20. The method of claim 14, wherein the second retina region comprises one or more of a macula region, a superior region, or a nasal region.

* * * * *